(12) United States Patent
Von Beichmann et al.

(10) Patent No.: US 9,261,524 B2
(45) Date of Patent: Feb. 16, 2016

(54) POSITIONING DEVICE FOR A SAMPLE DISTRIBUTION APPARATUS, SAMPLE DISTRIBUTION APPARATUS WITH POSITIONING DEVICE AND METHOD FOR POSITIONING

(75) Inventors: Boris Von Beichmann, Hamburg (DE); Uwe Mellenthin, Norderstedt (DE); Rainer Disselbach, Henstedt-Ulzburg (DE)

(73) Assignee: Eppendorf AG, Hamburg (DE)

( * ) Notice: Subject to any disclaimer, the term of this patent is extended or adjusted under 35 U.S.C. 154(b) by 1356 days.

(21) Appl. No.: 13/014,638

(22) Filed: Jan. 26, 2011

(65) Prior Publication Data

US 2011/0209564 A1 Sep. 1, 2011

Related U.S. Application Data

(60) Provisional application No. 61/301,157, filed on Feb. 3, 2010.

(30) Foreign Application Priority Data

Jan. 26, 2010 (DE) .......................... 10 2010 005 722

(51) Int. Cl.
*B01L 3/02* (2006.01)
*G01N 35/10* (2006.01)
*B01L 9/00* (2006.01)

(52) U.S. Cl.
CPC .............. *G01N 35/1011* (2013.01); *B01L 9/00* (2013.01); *G01N 35/1067* (2013.01); *B01L 9/523* (2013.01)

(58) Field of Classification Search
CPC ....... B01L 9/00; B01L 9/523; G01N 35/1011; G01N 35/1067
USPC .............................. 73/864.01, 864.23, 864.25
See application file for complete search history.

(56) References Cited

U.S. PATENT DOCUMENTS

| 4,235,971 A | 11/1980 | Boxer et al. |
| 4,473,213 A | 9/1984 | Decker |
| 4,478,094 A | 10/1984 | Salomaa et al. |
| 4,827,780 A * | 5/1989 | Sarrine et al. ............... 73/864.21 |
| 5,415,060 A * | 5/1995 | DeStefano, Jr. ................ 74/540 |
| 5,672,320 A | 9/1997 | Ritter |
| 6,199,435 B1 | 3/2001 | Wilmer et al. |

(Continued)

FOREIGN PATENT DOCUMENTS

| DE | 9218750 U1 | 4/1995 |
| DE | 4437716 A1 | 7/1996 |

(Continued)

*Primary Examiner* — Daniel S Larkin
(74) *Attorney, Agent, or Firm* — Todd A. Lorenz

(57) ABSTRACT

The invention relates to a positioning device for a sample distribution apparatus, such as a pipetting apparatus, providing a first part, at which a sample transport device can be arranged, a second part, at which a sample holder can be arranged, wherein the first part and the second part are arranged moveable in relation to each other between a first position and an adjusted target position of the first and second part for performing a positioning motion, such that a sample can be conveyed towards the sample holder by the positioning motion. The automated change of the target position assists for achieving an error-free positioning and sample distribution. A corresponding method for the automatical change of a position of a first part relative to a second part using the positioning device, is also claimed.

29 Claims, 28 Drawing Sheets

(56) References Cited

U.S. PATENT DOCUMENTS

| | | | |
|---|---|---|---|
| 7,597,854 B1 * | 10/2009 | Reynolds | 422/511 |
| 7,713,487 B1 * | 5/2010 | Locklear et al. | 422/501 |
| 2003/0017083 A1 | 1/2003 | Pobering et al. | |
| 2006/0110287 A1 | 5/2006 | Kraemer et al. | |
| 2007/0221684 A1 | 9/2007 | Steinbrenner et al. | |
| 2009/0095091 A1 | 4/2009 | Smith | |
| 2010/0252579 A1 | 10/2010 | Steinbrenner et al. | |
| 2011/0296930 A1 | 12/2011 | Deppermann et al. | |

FOREIGN PATENT DOCUMENTS

| | | |
|---|---|---|
| DE | 102008010267 A1 | 8/2009 |
| EP | 138205 B1 | 4/1985 |
| GB | 1456555 | 11/1976 |

* cited by examiner

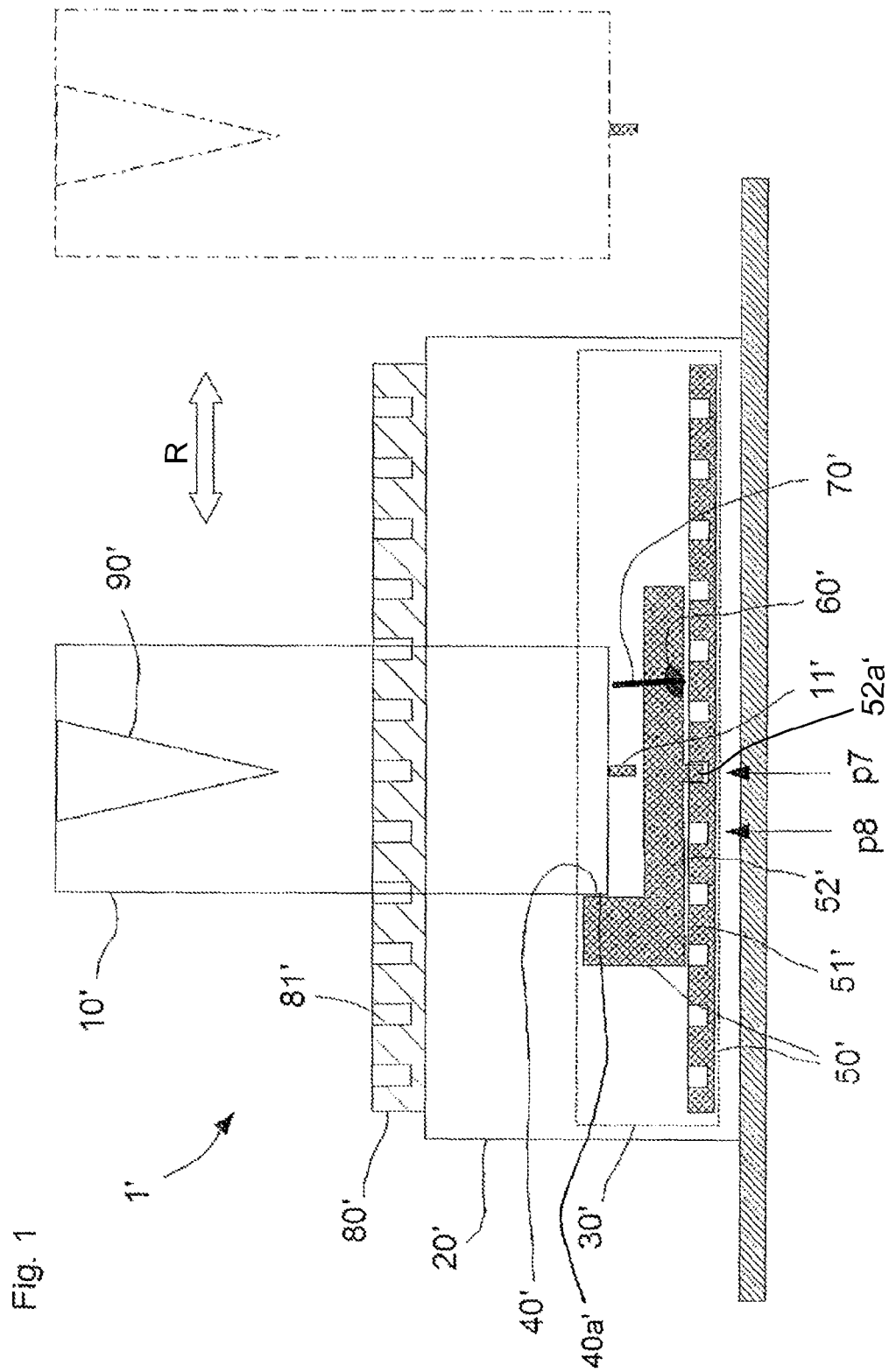

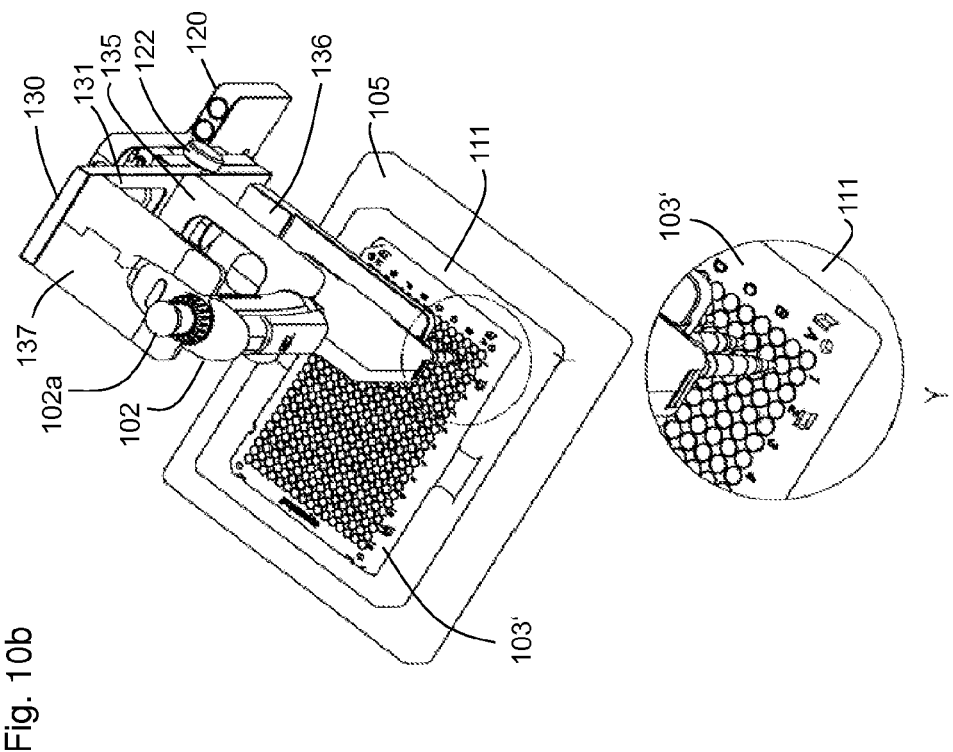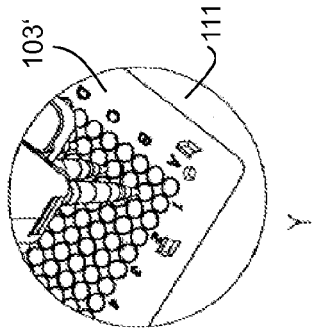
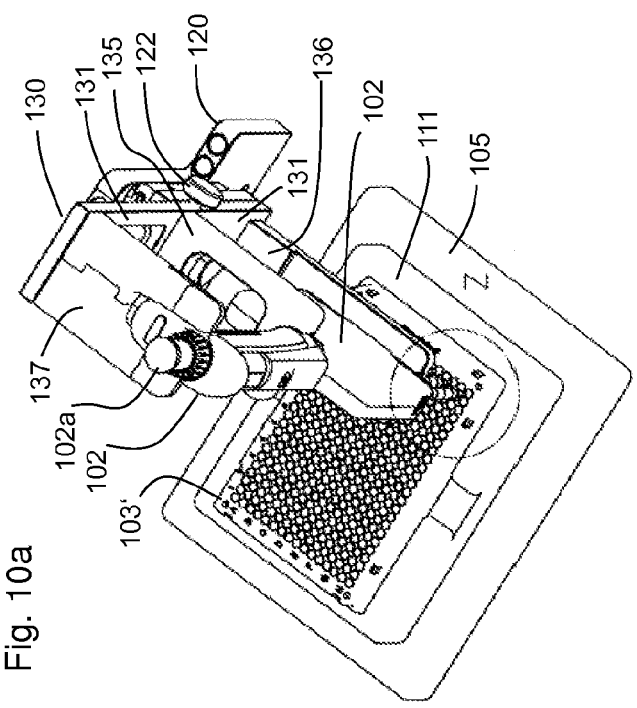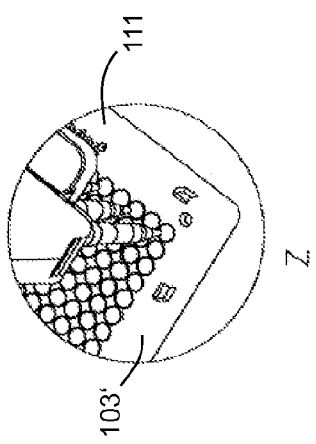
Fig. 10a
Fig. 10b

POSITIONING DEVICE FOR A SAMPLE DISTRIBUTION APPARATUS, SAMPLE DISTRIBUTION APPARATUS WITH POSITIONING DEVICE AND METHOD FOR POSITIONING

The present invention relates to a positioning device for a sample distribution apparatus, a sample distribution apparatus with a positioning device and a method for positioning.

Such apparatus are useful in laboratories to improve the efficiency of the procedures of distributing one or more samples to a plurality of sample receptacles, which are often largely processed manually. Apparatus, which are appropriate and known for a manual sample distribution are, for example, hand-operated pipettes and dispensers. A pipette is understood to be a device, wherein the sample volume, which is released by the device by a single operation, corresponds to the sample volume aspirated into the device, substantially. In contrast, in the case of a dispenser, the sample volume, which corresponds to several release doses, is released stepwise. Further, it is differentiated between single-channel devices and multi-channel devices, wherein single-channel devices only contain a single release channel and multi-channel devices contain several release channels, which allow the parallel release/uptake of the sample, in particular. Both kinds of devices allow for the manual distribution of samples to the sample wells, for example, of well plates with 96 or 384 sample wells, for example. The manual filling of the sample wells of a well plate requires that the user memorizes the sample well, which has already been filled, and which sample well is the next target. Hereby, errors can occur, for example, a missing filling, a wrong filling, or an unintended multiple filling of a sample well, because the filling status of a sample well is often difficult to be recognized, in particular, if transparent sample liquids are used, which provide a poor contrast against the well plate. By using a positioning device, which can be part of a sample distribution apparatus, for example in particular a pipetting apparatus, a higher throughput of the sample processing in a laboratory is possible, in particular if compared with a manual pipetting, which is useful for screening methods in microbiology and biochemistry, in particular.

An increased throughput of the sample processing is achieved by fully automated pipetting apparatus, in particular, at which uptaking of the sample, approaching the target positions and the release of the samples takes place fully automated.

For such apparatus, no predetermined or preadjusted target positions are required for approaching a target position, because a plurality of sensors, drives, appropriate control electronics and control programs, preferably, are provided, usually by means of which a target position is approached in a controlled manner. Thereby, however, the application of such automated apparatus is expensive and is often not thought to be an appropriate solution, if a medium throughput of sample processing is desired. Examples for such fully automated pipetting apparatus can be found in the EP 138 205 B1 or the U.S. Pat. No. 4,478,094, for example.

For a medium scale throughput in sample processing, for example for smaller or middle-sized laboratories, a manually performed sample distribution is desirable, which, however, is supported by means of a device. For such apparatus, means for an improved positioning of pipettes with respect to a sample holder, for example, are provided.

U.S. Pat. No. 7,597,854 B1, for example, describes a pipetting apparatus with assisting means, wherein the row of a well plate, which has to be filled, is covered from above by means of a slot-shaped aperture, wherein the sample release to the row takes place through the aperture slot. The aperture is connected to a guide rail, at which the aperture can be manually displaced in parallel to the well plate towards the respective target row. Marked locking positions facilitate the positioning and the discharge of the pipette at the position over a marked target row of the well plate for the user, which also is done manually. By means of marking the locking positions at the guide rail, which correspond to the row labels of the well plate, the filling of the sample wells is facilitated. However, if the user is not sure, whether the marked row is already filled or not, a wrong filling can take place at this apparatus, as the user fills the row of a well plate again, for example, without having displaced the aperture to the next target position before.

From U.S. Pat. No. 5,415,060, a pipetting apparatus is known, wherein a movable sample holder for holding a well plate with the respect to a fixedly arranged support bridge for supporting a manually supported pipette is displaced. Once the sample holder is placed at a release position with respect to the support bridge, a pipette filled with a sample can be approached manually to the support bridge by means of a separate process, can be supported to the same and the sample can be manually filled to the row of the well plate, which is marked by the support bridge. In a further, separate step, the sample holder is thought to be displaced manually to the next release position. This is achieved by letting the user move a lever, which is connected to a feed mechanism. The end position, at which the sample is to be released to the sample holder, is hereby reached only after finishing said displacement and adjusted. If the next row of the well plate is to be filled, the user has to memorize or to recognize, whether the actual position has been filled already or not filled, i.e. whether a change of position of a sample holder already has taken place or not. A further problem of this apparatus and of the manual filling of sample wells, in general, is that by the manual actuation of the pipette from the supply receptacle towards the target position of a well plate and back the user and the condition of the user greatly influences the constancy and reproducibility of the filling, and therefore, the error rate.

It is the object of the present invention to provide an improved positioning device for a sample distribution apparatus, in particular a manually operated sample distribution apparatus, an improved sample distribution apparatus with positioning device and an improved method for positioning, which, respectively, offer a sufficient throughput of the sample distribution and a sufficient error rate, in particular.

The object is solved by the positioning device according to the claims, the sample distribution apparatus according to the claims and the method for positioning according to the claims. Preferred embodiments are subject of the respective sub-claims.

The positioning device for a sample distribution apparatus according to the invention, in particular for a pipetting apparatus, provides: a first part, at which a sample transport device can be arranged, a second part, at which a sample holder can be arranged, wherein the first part and the second part are arranged moveable in relation to each other between a first position and an adjusted target position of the first and second part for performing a positioning motion, such that a sample in the sample transport device is conveyable in relation to the sample holder by means of the positioning motion between the first position and in the adjusted target position and is conveyable at the target position by a release from the sample transport device to the sample holder or is conveyable in the sample transport device in relation to the sample holder by means of the positioning motion between the first position and the adjusted target position by a motion of the sample transport device relative to the first part to a release position and is conveyable at the release position by release from the sample transport device to the sample holder, wherein an actuation motion is provided, which serves to convey the sample, a positioning auxiliary device, which provides at least one means for limiting of the relative mobility of the first and the second part at the adjusted target position, which preferably provides at least one means for adjusting of the n-th target position from a plurality of N predetermined target positions as the adjusted target position, which preferably provides at least one means for changing of the adjusted target position from the n-th target position to a (n+1)-th target position, and which further provides at least one first means for coupling of said actuation motion to said positioning auxiliary device or to its at least one means for changing, such that by means of the actuation motion the change from said n-th target position to said (n+1)-th target position can be effected via the position auxiliary device or its at least one first means for coupling.

The positioning device according to the present invention is preferably suitable to take over the decision of the user using a manually operated apparatus to decide which target position has to be approached in the next positioning step and is further suitable to facilitate the positioning of the first and the second part for the user. Therefore, the positioning device and the positioning auxiliary device according to the invention offer the advantage, in particular, that no additional user activity is required to change the adjusted target position, because the change of the target position takes place automatically upon the actuation motion. Using the automated change avoids the risk, in particular in the case of an at largest manually operation positioning device, that a user mistakes in estimating the status at a target position of a sample holder, such that the probability of a wrong or missing filling is reduced. However, the invention is also applicable in fully automated apparatus.

The actuation motion, preferably, is a manually performed motion by user, in particular along a horizontal direction, for example, a relative motion of the first and second part in horizontal direction, or in vertical direction. The actuation motion preferably is the positioning motion. By means of the positioning motion, the first and the second part are moved between the first position and the adjusted target position, wherein the positioning motion, preferably, provides a positioning forward motion in the direction of the adjusted target position and a positioning back motion away from the adjusted target position.

The actuation motion can also be a motion of the sample transport device relative the first part, in particular towards a release position or away from a release position, from which the sample is released from the sample transport device into the sample holder period. Preferably, said motion takes place in a vertical direction, in particular to change the distance between the sample transport device and the sample holder in an appropriate manner. In the release position, the distance between the sample transport device and the sample holder is reduced such that a safe release of the complete sample to the sample holder is guaranteed.

The actuation motion can also be effected automatically, for example by means of the action of an electromotor, in particular of a linear step motor, by an electromagnet or by another motor.

An actuation motion can effect the transfer of an electrical signal or influence an electrical signal, for example, if the positioning device comprises electronical means for the automatical detection of an actuation motion. The first means for coupling can comprise electrical means, by means of which said change of the adjusted target position from the n-th target position to a (n+1)-th target position is effected or triggered by detecting the actuation motion. Such electrical means can be designed for processing radio signals, for example, of radio frequency (RF)-signals. For example, the sample transport device can provide a shielded RFID-chip, whose shield is removed by means of the actuation motion temporarily, which can be electrically detected by means RF-radiation at least as an event. The actuation motion can also be in this case in particular preferred, the pressing of an actuation element, for example of a pipetting release button, at the same transport device by the user.

The change by means of the positioning motion being the actuation motion can take place in a preferred embodiment of the invention in particular in the case if the first and the second part are moved relative to each other in horizontal direction, which means, in the case that the actuation motion is a horizontal positioning motion. In the case of another embodiment according to the invention, the change can take place, in particular, if the first and the second part, or at least sections thereof, are moved relative to each other in vertical direction, which means in the case that the actuation motion is a vertical positioning motion. It is further possible and preferred that the actuation motion is such a motion, by means of which the release of sample from the sample transport device to the sample holder is achieved or triggered, for sample by means of electrical signal processing.

The adjusted target position, which is approached during the positioning motion, is preferably constructively predetermined, by providing means for adjusting the target position period. Moreover, the adjusted target position is already pending if the positioning motion to the n-th target position finishes. Preferably, the positioning device is configured such that the n-th target position is adjusted, before the positioning motion of the first and the second part towards the n-th target position is finished. Hereby, the positioning is facilitated and a more precise determination of the target position becomes possible.

Hereby, N is a natural number between two and infinite, preferably, and n<N, preferably. A position of the first and the second part refers to the relative position of the first and the second part to each other.

The first part and the second part of the positioning device are moveably arranged relative to each other, preferably along a linear direction R. Thus, it is possible and preferred, for example, that the sample distribution apparatus is stationary in space and that the first part of the positioning device is moveable arranged relative to the sample distribution apparatus and that the second part of the positioning device is arranged unmovable against the sample distribution apparatus (first preferred embodiment) or that the sample distribution apparatus is stationary in space and that the first part of the positioning device is unmovable arranged against the sample distribution apparatus and that the second part of the positioning device is moveable arranged against the sample distribution apparatus (second preferred embodiment). Having the first part, which can have attached a sample transport device, for example a pipette, moveable arranged and having a second part, at which a sample holder can be attached, for example a well plate, being arranged stationary and unmovable, achieves the advantage that open-top sample receptacles of the fixed sample holder do not have to be moved, such that the samples do not escape from the receptacles upon vibrations from the receptacles, which would lead to differing fillings and possibly would lead to cross contamination of receptacles, which are filled with different kind of samples. In contrast, the sample is located in a more and cased volume, preferably, for example in a pipette tip or a dispenser tip in the case that the sample transport device has to be moved, whereby such a sample storage is less sensible against the vibrations, which might occur during the motion period. Thereby, the sample distribution apparatus can also be non-stationary, respectively. Further, it is possible that the first and the second part are both arranged moveable against the stationary sample distribution apparatus such that both parts move during a positioning motion, for example. The positioning device according the invention is preferably characterized in that the first part is manually moveable relative to the second part by a user.

Preferably, and in particular in the case of the application at a non fully-automated apparatus, it is provided that the first part is manually moveable relative to the second part by a user or that the second part is manually moveable relative to the first part by a user. The first part and/or the second part provides at least one handle section, preferably, in particular one or two handle sections, at which the respective part can be handled by the user and can be moved against the other part, against the sample distribution apparatus or against the environment.

The positioning device according to the invention preferably provides a guiding device, by means of which a guided positioning motion of the first and the second part relative to each other can be performed between a starting position and a n-th target position. The guiding device can provide one or more guiding bar or guiding rail, which extend along the R-direction of the positioning motion. A guiding rail can provide a rail with a vertical cross section, which is T-shaped, L-shaped, U-shaped or I-shaped or shaped different, which can be fixedly arranged at the first or the second part. One or more guided elements can be substantially fixedly connected to the second or first part, to be guided during a positioning motion period. A guided element can be arranged such that it engages a guided rail at least in part formed closed, thereby providing a sufficient play for friction-efficient sliding. The guiding device is linear, preferably, to allow for a linear translational guiding motion (positioning motion).

The first position preferably is a position of the first and the second part, in which said parts are not yet located in the n-th target position. If the first and the second part are moved towards the n-th target position, the first position can be another target position, for example the (n−1)-th target position. The change from the n-th target position to the (n+1)-th target position as the adjusted target position preferably implies that a positioning motion, which was stoppable in the n-th target position by the n-th means for limiting of a plurality of N means for limiting or by a means for limiting with at least N possible positions, is stoppable in the (n+1)-th target position by the (n+1)-th means for limiting. Thereby, the N means for limiting can be geometrically arranged offset to each other, for example with increasing distance with respect to the first means for limiting. The change of the n-th target position to the (n+1)-th target position preferably implies that the (n+1)-th target position is adjusted temporally after the n-th target position.

The first position preferably is a starting position of the first and second part. Preferably, the first and the second part are farther away from each other in a starting position, or at least in part farther away from each other, than in a target position, related to a distance in a horizontal direction or vertical direction or another direction. A starting position preferably provides the possibility to take up a sample into a sample transport device in said starting position, for example by aspirating the same in the pipette tips of a pipette. A target position preferably offers the possibility to release the sample from the sample transport device to said sample holder in said target position.

A starting position is the position, preferably, in which the first part is arranged against the second part in a first distance, and a target position is that position, preferably, in which the first part is arranged against the second part in a second distance, which is different from said first distance. Said distance extends in a horizontal direction or in a vertical direction or in another direction, preferably.

The definition of the target- and release position can be such that a target position is that position, in which a dispensing device, which is arranged at the first or the second part for dispensing a sample transport device, is arranged against the second or first part in a first height, and a release position can be such a position, in which the dispensing device is arranged in a second height, which is different from said first height. The first height can be such that during the working operation of a sample distribution apparatus, which is provided with the positioning device, the performance of a natural relative motion of the first and second part, which is arranged in said first height, to the target position is possible. The second height can be such that during the working operation of a sample distribution apparatus, which is provided with the positioning device, the performance of a natural relative motion of the first and second part, which is arranged in said second height, is not possible. The positioning device can be configured such, i.e. provide corresponding constructive means, that the performance of a lateral relative motion of the first and second part in said first height is possible and/or in said second height is not possible.

The first and second part of the positioning device according to the invention can be moved to a plurality of N target positions, such that, for example, samples can be distributed to a plurality of target positions. N is a natural number larger than one and, preferably, is between 2 and 96, more preferably 2, 3, 4, 6, 8, 12, 16, 24, 32, 48, 64, 96 or, also larger than 96. It is even possible that the number of the target positions is not predetermined or limited, substantially, for example, by providing continuously variable target positions. A target position refers to a relative position of the first and second part to each other, preferably, and can, for example, refer to the position of a moveable first part at a stationary second part or to the position of a moveable second part against a stationary first part. A target position is, preferably, characterized by predetermined relative range of motion of the first and second part in a horizontal direction. Each target position n is, preferably, characterized by another, individual and predetermined relative range of motion of the first and second part in a horizontal direction.

Preferably, the predetermined target positions are constructively predefined by the positioning device, substantially, and can be chosen in dependence on a particular desired distribution pattern, in particular, which can correspond to the distances of sample vessels in a sample holder, for example, which can be the distance of the rows of sample vessels (wells) in a microtiter plate (well-plate).

However, it is possible and preferred that the predetermined target positions themselves are also choosable or configurable, by letting the positioning auxiliary device provide means for configuring the target position. This allows yet a larger flexibility of the application of the positioning device such that, for example samples can be distributed to configured patterns of distribution and distances of distributions. Thus, in pipetting apparatus with such a positioning device other sample holder can be used in addition, for example. For example, besides a 96- or a 384 well plate also well plates with a different number of sample wells and different distances of the sample wells can be used, in particular also non-standard sample holder.

Said means of limiting, means of adjusting and means of changing and first means for coupling are, preferably, mechanical means, respectively, and are acting mechanical, preferably, and, preferably, are not operated electrically, respectively. This offers the advantage and that are fully mechanical sample distribution apparatus can be realized, which provides such a non-electric positioning device, whose fabrication- and operation costs can be kept low and which can be used more flexible due to the independence on an electrical energy source. However, it is possible and preferred that at least one of said means or all means are configured to be operated at least in part electrically, or configured to be operated fully electrical, or provide electrically operated components. Moreover, the positioning device and/or the positioning auxiliary device can provide other means, which are configured at least in part to be operated electrically, are configured to be fully operated electrically or provide electrically operated components.

The positioning auxiliary device provides means for limiting the relative mobility of the first and second part in the adjusted target position, at least one means for limiting, which supports the positioning of the first and second part in said target position, in particular, by limiting or blocking a relative motion, in particular in horizontal direction, of the first and second part or of portions of the first and second part, preferably said positioning motion, upon reaching the adjusted target position. The means for limiting are configured, preferably, to limit the mobility of the first and second part at a target position in at least one direction, for example, by blocking a linear translatoric positioning motion, at which the first and second part are moved against each other, upon reaching a target position, while mobility in the opposed direction is preserved. However, it is also possible that the mobility is temporarily fully overridden, by providing, for example, a locking device, which locks the parts at a target position.

The means for limiting provide N interaction portions, preferably, which are assigned to the first and/or the second part, wherein the n-th interaction portion causes a limitation of the mobility of the first and second part in the n-th target position by interacting with a counter portion, which is provided at the second or first part, preferably. An interaction can be mechanically, for example, can provide an attachment or a locking, or can also be non-mechanically, for example, can be a magnetic interaction. An interaction portion can be a separated section of a component, for example, a side of the component or a clearly defined face of the component, or can be a portion of a continuously changing section of the component, for example a position on a ramp-like surface.

The N interaction portions are, preferably, arranged spaced apart from each other. Preferably, the n-th interaction portion is arranged in a fixed distance A to the nearest (n+1)-th interaction portion, in particular also to the nearest (n−1)-th interaction portion. A can be the same for all for multiple interaction portions, or can be different for all or multiple interaction portions. The interaction portions are, preferably, arranged along an open distance, for example along a straight line, or along convoluted line, for example a winding, a helix, a coil, a loop or a circle. The convoluted line offers the advantage that the change from the N-th target position back to the 1-th target position is technically easier to realize, because a motion, which is required for the change of the N-th interaction portion to the 1-th interaction portion as the adjusted interaction portion, in this case it can be performed more easy, generally, than in the case of an open distance. Preferably, the interaction portions are arranged equally spaced, for allowing the distribution of the samples to periodically arranged target positions, in particular, to grid-like arranged target positions, in particular the sample vessels of a well plate at a second part.

Preferably, the interaction portions are connected to the second part, preferably, or are connected with the second part moveable in one direction, preferably, in the direction of the straight line, a circle or a helix. In particular, the interaction portions are pivotable around an axis, which is fixed to the second part. However, it is also possible and preferred, that the arrangement of the interaction portions is changeable, in particular manually changeable by a user, or automatically changeable, for example, by means of an electric control, or by said means for configuring the target positions. Thereby, a higher flexibility of the positioning device is achieved, which, in this way, can be configured for the distribution of a sample or multiple samples to changeable target positions, in particular.

An interaction portion can be, for example, a stopping portion or a locking device or a part of a locking device. Preferably, the means for limiting provide the plurality of N stopping portions, at which the motion of the first and second part is stoppable in a direction of a motion by the attachment of both parts against each other, or, for example, also is blockable, lockable or brakeable, if said parts are guided from a first position in the direction of a target position. Preferably, a target position is assigned to each stopping portion, such that by the attachment of the n-th stopping portion, which, for example, can be arranged at the second part, against a counter stopping portion, which, for example, can be arranged at a first part, the n-th target position can approached. Preferably, a counter stopping portion, which is arranged at the first part, preferably, is assigned to the positioning auxiliary device such that the attachment of the n-th stopping portion to said counter stopping portion stops the relative motion of the first and second part. The positioning auxiliary device, preferably, provides means for the manual adjustment of the position of the counter stopping portion with respect to the first or second part. A stopping portion can be a flat surface, a sloped, ramp-like surface with a linear or a non-linear slope, which can be adjustable, in particular, or can provide a surface with a roughened or a sawtooth-like characteristic, whereby the interaction with a counter stopping portion, which has a similar structure, can be increased, by achieving a locking of the attaching surfaces on a microscopic or macroscopic scale.

However, it is possible that the means for limiting stop or block or also only limit the related motion of the first and second part at a target position by providing a locking device in the interaction portion, for example, by means of which the mobility of the first and second part at a target position is not fully overridden but only limited. For example, a resistance device can be provided, which can comprise a brake element within a guiding device, which acts on the mobility of the first and second part at the target position, and by means of which, in particular, the positioning motion is constricted by a resistance upon reaching of the target position and, thus, the target position is detectable by detecting the mobility, for example, is sensible by a user.

The means for limiting can also provide electrical control components, such as for example electrical circuits, a (programmable) electrical digital and/or analogue control, or a program code, which serves to the function of limiting the mobility of the first and second at a target position. Further, the means for limiting can provide (electro-)magnetic means, by means of which the mobility of the first and second part at a target position can be limited for blocked period.

The positioning device should allow the positioning in more than one target position. Therefore, the positioning auxiliary device provides at least one means for adjusting the n-th target position from a plurality of N predetermined target positions as the adjusted target position. Preferably, said means for adjusting provide a locking device, by means of which each adjustable target position can be at least temporarily maintained by locking, to prevent that an adjusted target position can be displaced by mechanical vibrations, gravity effect and the like. A target position can also be configured chooseable, for example by an operating person or by an automatic control, and is adjusted before reaching the target position as the "adjusted target position", in particular before performing a corresponding positioning motion.

The means for adjusting are, preferably, arranged at the first part or the second part. Alternatively, they are connected unmovable with said first or second part, preferably, at least in part connected unmovable, in particular, fixed to said first or second part in part or fully rotatable, or of fully or at least in part fixed, at least temporarily, so said first or second part, wherein "fixing" can mean the fixing in at least one direction, in particular the fixing in all directions.

The means for adjusting preferably provide a main element, at which, preferably, the means for limiting and the means for changing are arranged, in particular, at least in part. Further, it is possible that the means for adjusting provide at least one auxiliary element, which can be a component, which is integrally connected to the main element, for example, or is a separate component. The auxiliary element can be arranged moveable against the main element, in particular, translatorically displaceable or rotatable against the main element, in particular be connected to the main element as the part of a kinematic change. The means for limiting can be arranged at the auxiliary element.

It is possible and preferred that the main element is a locking element, which carries N interaction portions, for example locking portions. The auxiliary element can be a component, which is configured for a stepwise locking to each locking portion, at which a means for limiting can be arranged, for example a stopping portion.

An auxiliary element can provide a solid or variable shape, and can, for example, be increasable or decreasable in a telescopic manner. By such a variable shape, higher flexibility is achieved, because more target positions can be realised. For example, an auxiliary element or the main element of the means for adjusting can provide a ramp-like characteristic, and can be arranged at the main element or at the first or second part, in particular, such that a counter portion attaches to a different position of said ramp depending on the positioning against said ramp, in order to realise another target position, respectively. A ramp-like or continuous characteristic allows, in particular, the realisation of more than one fixed numbers of N predetermined target positions. The main element or the auxiliary element can be configured to generate a slope of the ramp which can be manually or mechanically or automatically changed, to realize a changeable number of target positions or a changeable distance of the target positions.

The means for adjusting, preferably provide a component, which is rotatable around a rotation axis, which is preferably arranged to be translatorically unmovable against the first or second part, or is arranged translatorically moveable against at least one part. The rotatable component, preferably, forms said main element of the means for adjusting. Preferably, the means for adjusting are arranged along a closed distance at the main element, the distance being arranged around the rotational axis. At least one auxiliary element can be provided at the rotatable component, in particular N auxiliary elements, which can be arranged along a circle, which has its centre within said rotational axis, at a front side of the rotatable component. Each auxiliary element can carry an interaction portion.

The rotatable component can be a drum device, at which are arranged, preferably, said means for adjusting and said means for changing, at least in part. The positioning device according to the invention is characterized in that, preferably, said means for adjusting are arranged at said second part and comprise, in particular, a rotatable drum device, at which, preferably, the means for limiting and the means for changing are arranged at least in part.

The drum device, preferably, provides a substantially cylinder-shaped or hollow-cylinder-shaped base body, whose rotational axis is pivoted at the first or second part, preferably. Preferably, at least one auxiliary element is provided, in particular N auxiliary elements, for example twelve auxiliary elements, which are arranged at a front side of the drum device along a circular distance along the rotational axis at the drum device, in particular spaced apart from each other in equal distances, and which are in particular, fixed to said drum device. An auxiliary element can be an elongated component, which means a component, whose length is larger than its width and height, respectively, in particular at least twice, three times for four times larger. An auxiliary element can be shaped, respectively preferred, and also in combination, pin-like, rod-like, cylinder-like, grid-like, ring-shaped, ring segment-shaped, ramp-like can be shaped different. One or multiple means for limiting, for example a stopping portion, can be arranged at a front side of the auxiliary element, to define a target position upon attached of a counter stopping portion.

The positioning device according to the invention is characterized in that, preferably, the positioning auxiliary device provides means for the manual adjustment of the n-th target position from a plurality of N predetermined target positions. Thereby, the adjusted target position cannot only be changed automatically or stepwise, but the target positions can also be approached manually or automatically in dependence on a changing mechanism. Such means for manual adjusting are preferably configured mechanically or electrically, and can provide a adjustment wheel with means for marking for marking of the adjusted target position, wherein the adjustment wheel can be, in particular, connected with the rotatable component, in particular to said drum device, via a rotating rod, such that the drum device is directly rotatable by means of said adjustment wheel.

The positioning auxiliary device provides at least one means for changing, in particular for automatical changing, of the adjusted target position from the n-th target position to a (n+1)-th target position. By the changing, preferably, an alteration of the range of the relative motion of the first and second part in a horizontal direction is achieved. Further, a stepwise altering of the adjusted target position is effected, preferably, by changing to a new target position prior to each new step or after each new step "automatically", i.e. for example without additional user activity. The change from the n-th target position to the (n+1)-th target position as the adjusted target position implies, preferably, that a positioning motion, which in the n-th target position was stoppable by the n-th means for limiting from a plurality of N means for limiting or by a means for limiting with at least N possible positions, is stoppable in the (n+1)-th target position by the (n+1)-th means for limiting. Thereby, the N means for a limiting can be arranged with increasing distance with respect to the first means for limiting geometrically spaced apart to each other, for example. The n-th target position can also correspond to a position of the n-th means for limiting, which is geometrically predetermined or can be predetermined. However, it is also possible that said change from the n-th target position to the (n+1)-th target position as the adjusted target position implies that a positioning motion, which in the n-th target position was stoppable by the n-th means for limiting from a plurality of N means for limiting or by a means for limiting with at least N possible positions, is stoppable in the (n+1)-th target position by another means for limiting than the (n+1)-th means for limiting. This case occurs, for example, if a user intermediately has set an arbitrary (n+m)-th target position, wherein m is a natural number larger than zero, by means of a manual means for adjusting, by means of which an alteration of the adjusted target position can take place, preferably, with an arbitrary increment.

The means for changing can comprise a ratchet device (for example, a frictional locking mechanism or a ratchet wheel), which in particular allows the motion of the first and the second part in one direction, for example in the direction of the positioning motion, by one step and which locks against the direction of motion, or which allow in particular the rotation of the rotatable component according to a step distance in one permitted direction and prohibit or hinder the rotation in locking direction. Means for changing can comprise at least one projection, at least one recess or at least one groove, which can be arranged at the surface of the means for adjusting, in particular of the drum device.

The positioning device according to the invention is characterized in, preferably, that said drum device provide a substantially cylinder-shaped outside and said means for changing provide in particular a plurality of N helical guiding grooves or slotted links, whose ends, which are preferably open, are directed into the direction of the rotation axis of the drum device.

The positioning auxiliary device further provides at least one first means coupling of said positioning motion to said positioning auxiliary device or for coupling of said positioning motion to said means for changing such that by the first means for coupling the change from said n-th target position to said (n+1)-th target position can be effected during a positioning motion. First means for coupling can provide one or more projections, latches, rods, plates, actuators, engagement elements and/or other components, which can be moveable and/or unmovable connected with each other, and which can be arranged at the first or second part. Preferably, the first means for coupling are arranged and configured such that a positioning motion, in particular a positioning forward motion or a positioning backward motion lead to an interaction (mechanical, magnetically, electrically etc.) of the first and second part automatically, i.e. in particular without additional user activity, in particular leads automatically to a change from the n-th target position to said (n+1)-th target position as the adjusted target position.

The positioning device according to the invention is characterized in, preferably, that the first means for coupling comprise an engagement element, which is arranged at the first or second part, which is moveable arranged at the first or second part, in particular in a engagement direction, which is perpendicular to the rotation axis of a rotatable component, in particular of the drum device, and which is preferably arranged in the direction of the rotation axis unmovable at the first or second part, and which is configured for the engagement into at least one or each of said guiding grooves (of the drum device). Further, the positioning device according to the invention is characterized in, preferably, that said first means for coupling are mechanical such that they mechanically effect the change from said n-th target position to said (n+1)-th target position during the positioning motion. The positioning device according to the invention is characterized in, preferably, that said first means for coupling are arranged moveable at the first or second part and that the positioning auxiliary device also provides second means for coupling of the positioning motion to the first means for coupling such that the first means for coupling are moveable by the second means for coupling during a positioning motion. Preferably, the first means for coupling are arranged at the first part of the positioning device.

Preferably, the positioning auxiliary device also provides at least one second means for coupling the positioning motion to the first means for coupling such that the first means for coupling are moveable by the second means for coupling during a positioning motion.

The positioning device according to the invention is characterized in, preferably, that the guiding device is configured for performing a translatoric relative motion of the first and second part along a linear guiding direction, which extends in parallel to the rotational axis of the drum device, substantially, such that the engagement of the engagement element into the guiding grooves of the drum device effects that the engagement element, which engages a guiding groove, turns the drum device upon a substantially translatoric positioning motion, whereby a change from the n-th target position into the (n+1)-th target position occurs, wherein the latter is adjusted as said new adjusted target position.

The positioning device according to the invention is characterized in, preferably, that the at least one second means for coupling is configured for moving the engagement element along the engagement direction, whereby said means contain a slotted link device and a slide block member, whereby, preferably, the slotted link device is arranged at the second part and/or is arranged extending substantially along the linear guiding direction and wherein the slide block member is arranged substantially perpendicular to the engagement direction and substantially perpendicular to the rotational axis at the engagement element.

The positioning device according to the invention is characterized in, preferably, that said slotted link device provides a slotted link or multiple slotted links, and said slide block member provides one (or multiple) slide blocks, which can be guided by the slotted link (or by multiple slotted links), wherein the slotted link is shaped such that the engagement element does not engage the guiding groove during the positioning motion from the starting position to the n-th target position and engages into said guiding groove during the positioning back motion from the n-th target position to the starting position, wherein during said returning motion the change from the n-th target position to the (n+1)-th target position occurs, which is adjusted as said new target position. Vice versa, the engagement element can engage into the guiding groove also only during the positioning forward motion, thereby changing the target position. Preferably, the slotted link device provides an elongated, in particular substantially linear, run, wherein a substantially linear slotted link, preferably, provides a first and, in particular, also a second end region and a middle region, which provides a larger width than an end region.

Preferably, the sample distribution apparatus provides a deactivation device, by means of which it can be prevented that the actuation motion effects the change from said n-th target position to said (n+1)-th target position via the first means for coupling. This offers the advantage that the sample distribution apparatus can be applied more flexible, by allowing to perform the actuation motion by the activation of the change automatic also in such a way that it does not mandatory effect the change from said n-th target position to said (n+1)-th target position, in particular, temporarily or until the anewed activation of the change automatic. Preferably, said deactivation device is operable manually or automatically, for example program controlled. A second operation mode can be provided, where the change automatic is deactivated by the deactivation device, while it is activated during the first operation mode. For example, a user can decide by means of said deactivation device to initially utilize the sample distribution apparatus in the first operation mode and to switch temporarily to the second operation mode, to, for example, manually modify the filling of a sample plate, which was modified during the first operation mode. The deactivation device can provide a dead mans control, such that said first operation mode is the standard mode. The deactivation device can be configured such that the effect of the first means for coupling or said second means for coupling is prevented during the activation function by having the deactivation device provided with corresponding mechanical and/or electrical or otherwise acting means. For example, the deactivation device can provide a lever, which—in the case of the activation—guides said slide block member during the positioning motion to bypass the slotted link, such that said engagement element does not engage the guiding groove of said drum device such that said change is not automatically effected.

The positioning device according to the invention is characterized in, preferably, that spring means for suspending of the relative motion of the first and second part are provided, if the relative motion approaches the n-th target position. Thereby, it is prevented, for example, that an impetuous attachment of the first and second part occurs, which increases the lifetime of the parts are maintains the position of the positioning device, respectively, and prevents that, for example, a liquid sample is released to an undesired position from a sample transport device upon reaching the target position. The spring means can provide elastic elements, for example springs like coil springs, leaf springs or buffers from an elastic material, for example, rubber, or attachment damping devices, which, for example, work on magnetic basis. Thereby, it should be noted that a high precision of the positioning of the first and second part is important, which in addition should be long-term reliable, such that the corresponding spring means should be chosen appropriate.

The sample distribution apparatus according to the invention is, in particular, a pipetting apparatus, which, preferably, provides a positioning device according to the invention.

The sample distribution apparatus according to the invention, in particular, provides a positioning device, which, in particular, is configured according to the invention, wherein the positioning device provides a first part, at which a sample transport device can be arranged, a second part, which is moveable arranged relative to the first part, wherein a sample holder can be arranged at the second part, and a guiding device, by means of which the first and the second part can repeatedly be guided in relation to each other between a first position and an n-th target position, wherein the sample distribution apparatus further provides, preferably: a supply container holder which is suitable for holding a supply container, which is filled with a sample, in a predetermined height, and, preferably, means for altering the height of the supply container holder in relation to said first part.

The sample distribution apparatus according to the invention is characterized in, preferably, that it provides a third means for coupling the relative motion of the first and the second part, in particular the positioning motion, and that said at least one means of altering a height of the supply container or supply container holder are provided such that by means of said at least one third means for coupling an alteration of the height of the supply container is effected during the relative motion, in particular during the approaching of a starting position. Such a supply container lifting automatic offers the advantage that in particular no additional user activity is required to arrange a sample uptake position, in which the sample can be taken up from a supply container into the sample transport device, whereby the efficiency of the sample distribution apparatus is increased.

The sample distribution apparatus according to the invention, which, in particular, provides a positioning device according to the invention, can be a pipetting automat, a pipetting robot, a pipetting-semi automat, or a pipetting apparatus, which can, in particular, be manually operable or actuable, which, respectively preferred, can be operated automatically, semi-automatically, electrical, partly electrical, fully or at least in part hydraulic or pneumatically, fully mechanic or combined mechanic, hydraulic, pneumatic and/or electrically configured. Preferably, the sample distribution apparatus is a manual actuable apparatus, which is usable, in particular, without an external electrical energy source. Thereby, an advantage is achieved compared to a fully automatic electric sample distribution apparatus, for example a pipetting robot, which is that it can be operated off-the-grid, which allows for a more flexible use. Further, the dimension and the mass of the sample distribution apparatus can be kept low by the more simple embodiment, the sample distribution apparatus being arranged, for example, within a volume smaller than 60 cm*50 cm*40 cm or 50 cm*40 cm*30 cm (width*height*depth) or, for example, providing a mass of less than 3 kg, 5 kg, 8 kg, 10 kg, 12 kg or 15 kg. A smaller footprint or mass also allows a more flexible application of the sample distribution apparatus, which thus can be arranged, for example, on the most laboratory-working surfaces (work benches) and can be easily displaced.

The sample distribution apparatus preferably provides a housing, which encases in particular a positioning device according to the invention, substantially, or at least partially encases the same. The housing is configured for a stationary arrangement, and, for example, provides rubber sockets or the like for a solid stand on a laboratory work bench, for example. Further, a stage can be provided, which carries components of the positioning device.

The positioning device and the sample distribution apparatus and their components can be fabricated, preferably, by metals, for example, aluminium or steel, to achieve a rather high precision and a long term stability. The positioning device and the sample distribution apparatus and their components are, moreover, preferably fabricated by plastics, for example, by polypropylene. Preferably, the positioning device and the sample distribution device and their components are fabricated by such materials, which guarantee a corrosion resistance, in particular, if aqueous samples are used, in particular biological media, which can contain salt. Said materials should, preferably, be chemically inert, and be treatable by cleaning substances substantially without influencing their composition, which allow sterilizing of the components, for example by a 70% alcohol/water-mixture, which are used for the sterilization of sterile working areas in biological or medical research laboratories. Moreover, the parts of the positioning device and the sample distribution apparatus can provide coatings, to achieve said characteristics. In particular, the surfaces are anodized, to provide them with an oxide layer by means of an electrolytical procedure, which is based in particular on anodic oxidation. This can be done, in particular, in the case of parts made of aluminium.

The sample distribution apparatus is, preferably, configured for the application with a common pipette, in particular multi-channel pipette. Examples for suitable and preferred multi-channel pipettes are the multi-channel pipettes Eppendorf Research®, and Eppendorf Research® plus, for electronical pipettes the pipettes Eppendorf Research® pro and Eppendorf Xplorer® of the Eppendorf AG.

Moreover, the sample distribution apparatus according to the invention can be utilized with dispensers, such as for example the dispensers Multipette® and the electronical dispensers Multipette® stream and Multipette® Xstream of the Eppendorf AG.

However, it is also possible and preferred that the pipette is especially configured for the utilization with a sample distribution apparatus according to the present invention, and can be configured for the exclusive application and/or integration into the sample distribution apparatus.

A multiple pipette, which is preferably suitable for use with the sample distribution apparatus according to the invention, preferably provides 2, 4, 6, 16, 24 or, especially preferred 12 or, even more preferred, 8 channels. Such multiple pipettes are particularly suited for the filling of commercial well plate or other well plates. An eight channel pipette can, in particular, be used for filling of 96-, 384- or 1536 well plates.

Convenient well plates are other well plates provide, respectively preferred, 96 or 384 sample wells, or preferably 4, 8, 12, 16, 32, 64, 192, 1536, 6144 or another number of sample wells. Suitable known well plates are, for example, the Eppendorf Plate® polypropylene with 96 or 384 sample wells, or the Eppendorf Deepwell Plate® with 96 or 384 sample wells of the Eppendorf AG, respectively independent on the shape of the bottom of the wells. The well plate, as described, are preferably provided for the application in the sample distribution apparatus, even though other sample holder with multiple sample containers (for example, sample wells), which are connected with each other, or for holding of single sample containers, for example, sample tubes, are possible.

Preferably, the sample distribution apparatus provides a sample holder arrangement section, which can provide a sample holder adapting plate. The sample holder adapting plate can be configured for accepting one (or multiple, in particular different) sample holder, or can be configured for the simultaneous or non-simultaneous acceptance of multiple, in particular different, sample holders. For that purpose, an adapter device and/or a connection device for connection with an adapter device can be provided, wherein by means of an adapter device, for example an adapter frame, a particular type of sample holder can be suspended, for example, different types of well plates or of integrally with each other connected sample vessels or by plugging of connected sample vessels, for example in the form of sample vessel stripes. Preferably, a pipetting apparatus provides a section, which is configured for holding of pipette tips or for holding of a pipette tip supply holder. A pipette tip supply holder preferably provides a stage with an aperture plate, in whose apertures the pipette tips are stored, preferably such that a single perpendiculary guided motion of an unequipped multi-channel pipette can equip the same completely with pipette tips. Said section can be configured in a cover plate of the housing of the pipetting apparatus, in particular as a recess, and in particular in the sample holder adapting plate.

The sample distribution apparatus according to the invention can, however, not only be used with pipettes, but also with other sample transport- or sample dosing devices, which, for example, convey sample-volumina by application of pumps or gravity. The sample to be distributed is liquid, preferably, but can also provide another consistence, and can be, for example, gel-like, powder-like, solid or gaseous.

Preferably, the sample distribution apparatus provides a height adjustment device, which is, preferably, mounted or mountable to the first part, or is user separable connected to the first part or not separable, and by means of which the height of a sample transport device, which can be connected to the height adjustment device, can be adjusted relative to the first and/or second part. This way, the optimum release position, in particular, or, uptake position can be determined at the sample distribution. The height adjustment device preferably provides a third and, preferably, also a fourth part, which is (or are) moveable arranged against each other or against the first part. Preferably, the height adjustment device provides a guiding device, by means of which the relative motion of the third and, if provided, the fourth part is guidable in the guiding direction, in particular substantially in said direction, i.e. in vertical direction. Preferably, the third part, and, if applicable, the fourth part, are holding devices for the sample transport device, for example support elements.

The height adjustment device can provide spring means for the suspension of the motion of the third and, if applicable, the fourth part, to prevent impacts due to a to impetuous attachment of the parts, and prevent, in particular, an undesired leaking of liquid samples. The spring means for suspension can comprise elastic elements, for example springs, in particular coil- and leaf springs, buffer from an elastic material, such as rubber, or attachment damping devices, which, for example are based on magnetic effects. Thereby, it should be noted, that preferably a high precision of the positioning of the third, and, if applicable, the fourth part is important, which moreover should be long term stable, such that the used spring means for suspensions should be chosen appropriately.

The lift of the height adjustment device is preferably dimensioned such that a positioning of sample transport device for the uptake of samples is possible from different kind of suitable sample supply containers and for the release to different types of sample holders. The height adjustment device preferably provides a quick adjustment device, such said predetermined heights, which can be adapted to the height of standard well plate or the length of standard pipette tips, can be directly and easy adjusted by the user substantially without a laborious height control. For example, this way, a lift between 0.5 and 100 mm, 1 mm and 10 mm, 3 mm and 50 mm, 3 mm and 20 mm, or in particular, of 4.5 mm or 9 mm can be definable, to be able to quickly adjust the third and, if applicable, the fourth part against the first part for approaching a 96- or 96 well plate.

The sample distribution apparatus in particular provides a holding device for holding a sample transport device, in particular a pipette holder, which is preferably connected to the first part and is preferably separable and connectable by a user. Different holding devices can be provided for holding different sample transport devices, or a single holding device can be provided, which can be configured for holding different sample transport devices. Preferably, a connection device is provided, by means of which the holding device is connectable with the first or second part, in particular pivotable connected.

Preferably, the sample distribution apparatus provides an inclination device, by means of which said holding device for holding the sample transport device is arrangeable against the vertical direction (z direction) in an angle $0°\leq\alpha\leq90°$, wherein preferably $1°\leq\alpha\leq10°$ or $1°\leq\alpha\leq5°$. The inclination allows to release a sample not only in a perpendicular downward direction. For example, it allows a user to release a sample by means of the pipette tips to the lateral inner wall of a vessel.

This is advantageous for small sample volumina, if the sample weight cannot overcome the adhesion of the drop to the pipette tip, to drop downwards in a defined way. The inclination device preferably provides an inclination axis, which is substantially arranged horizontally, for example an inclination axis, which rotatable connects the third and the fourth part. The inclination axis can be realized by a metal pin, which can be, for example, mounted to the first part and which can extend through an opening of the third or fourth part rotatably. Preferably, the inclination device provides means for fixing the inclination position, for example, a fixing wheel. Further, the decline device preferably provides means for an automatic returning to the vertical position period. Thereby, for example, a third part, which is rotatable against the first part, is automatically set back to the vertical position upon being released by the user. The means for the automatical returning can comprise a spring like a spiral pull-spring, which pulls back the third part to the vertical position, for example, if the user stops to incline the third part.

Preferably, the sample distribution apparatus provides an automatic height adjustment device, at which a height adjustable component of the apparatus is automatically height adjusted by the actuation motion, in particular by the positioning motion. Said component is preferably a height adjustable sample supply container holder, such that different sample supply containers are usable with the sample distribution apparatus and/or a comfortable sample uptake is allowed, by automatically lifting the sample supply container in the direction of the sample transport device. For said purpose, the sample distribution apparatus preferably provides means for altering the height of the (sample-) supply container holder in relation to said first and/or second part, for example, a (for example automatic) lifting device with one or more lifting elements, which can comprise a roller and/or a taper key element.

The method according to the invention for positioning a first part relative to a second part in subsequent steps at respectively different target positions by means of a positioning device, which is in particular configured according to the invention, in particular in a sample distribution apparatus, which in particular is configured according to the invention, in particular in a pipetting apparatus, comprises the steps, that an n-th positioning motion of the first and second part relative to each other between first position, preferably the starting position, and a predetermined n-th target position is performed, which can be adjusted as a one of N possible predetermined target positions at the positioning device, that a proximate (n+1)-th positioning motion of the first and second part relative to each other is automatically performed between a first position, preferably a starting position, and the (n+1)-th target position, by using a positioning motion for the purpose to effect the change from the n-th target position to the (n+1)-th target position by the coupling of the positioning motion with a positioning auxiliary device, such that the latter is adjusted as the new adjusted target position.

The method according to the invention preferably comprises the feature that the return path of the n-th positioning motion from said n-th target position back to a first position, preferably to the starting position, is used to effect said change from the n-th target position to the (n+1)-th target position by means of a coupling of the positioning back motion to a positioning auxiliary device, such that the (n+1)-th target position is adjusted as said new adjusted target position. Here, alternatively, the positioning forward motion can be utilized as well.

The invention also relates to a positioning device for a sample distribution apparatus, in particular a pipetting apparatus, which provides: a first part, at which a sample transport device is arrangeable, a second part, at which a sample holder is arrangeable, wherein the first and the second part are arranged moveable relative to each other between a first position and an adjusted target position of the first and second part for performing a positioning motion such that a sample is conveyable against the sample holder by the positioning motion between the first position and the adjusted target position and is conveyable at the target position by release from the sample transport device to the sample holder or is conveyable in the sample transport device against the sample holder by the positioning motion between the first position and the adjusted target position and by a motion of the sample transport device relative to the first part into a release position and is conveyable at the release position by release from the sample transport device to the sample holder, wherein an actuation motion is provided, which serves to convey the sample, wherein by means of said actuation motion a further effect is automatically achieved, which is, for example, the automatical change of the adjusted target position or the automatical height adjustment, for example of a sample supply container holder.

The definitions of terms and explanation of components and means are valid for all subjects according to the invention, i.e. the positioning device, the sample distribution apparatus and the method, if it is not described different or if it is not to be derived different from the context. Features of the subjects and embodiments according to the invention can also be combined, where it seems possible or advantageous.

Further preferred embodiments of the positioning device according to the invention, of the sample distribution apparatus according to the invention and of the method according to the invention can be derived from the subsequent description of the embodiments with reference to the figures and their description. Same components of the embodiments are substantially represented by the same reference numbers, if it is not described different or if it cannot be derived different from the context. It is shown:

FIG. 1 shows a first embodiment of the positioning device according to the invention.

FIG. 2 to FIG. 16b show an embodiment of the sample distribution apparatus according to the invention, which provides a positioning device according to the invention in a second embodiment, as well as different subcomponents of the sample distribution apparatus and suitable accessory in preferred embodiments.

Figure 2A:
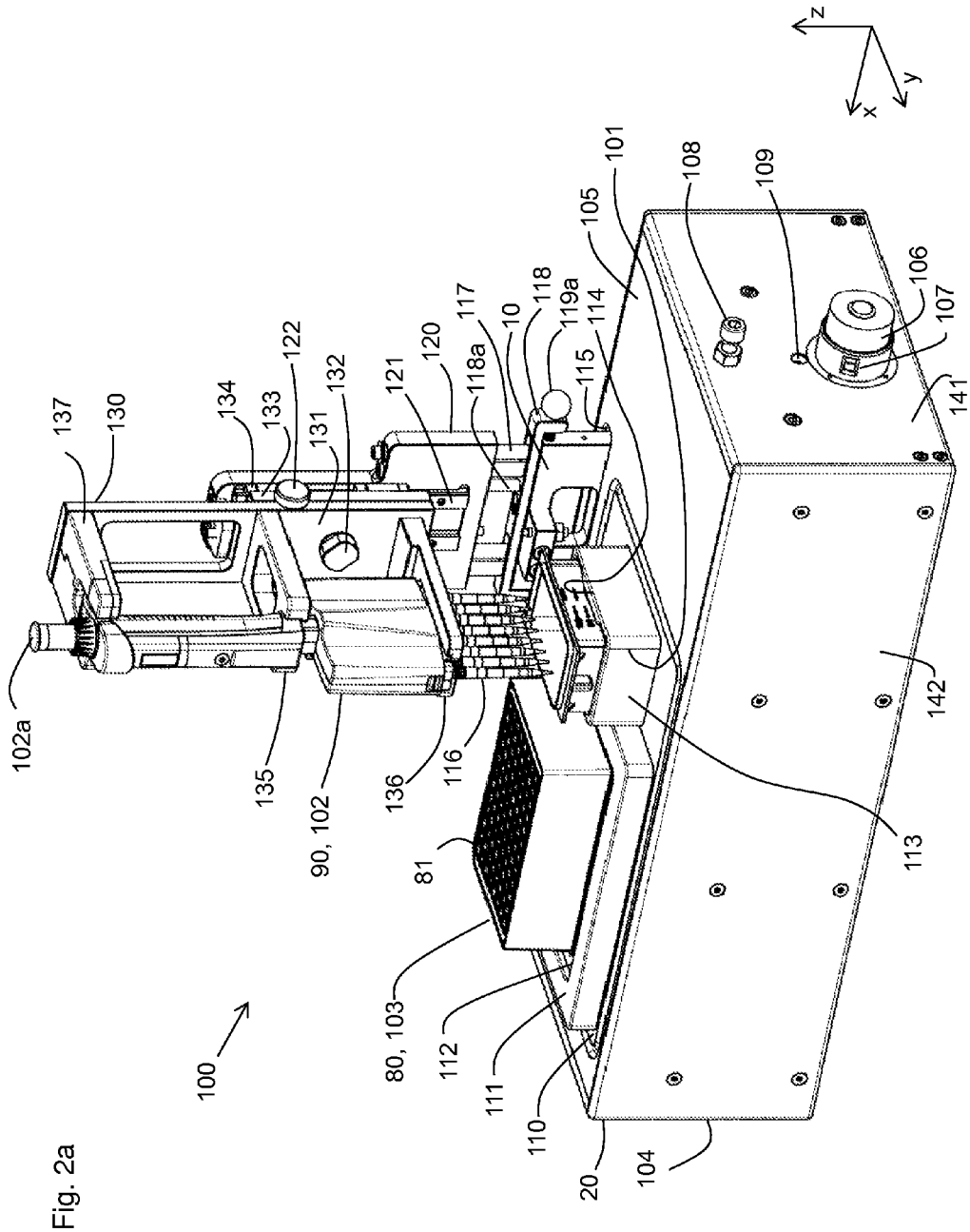
Figure 2B:
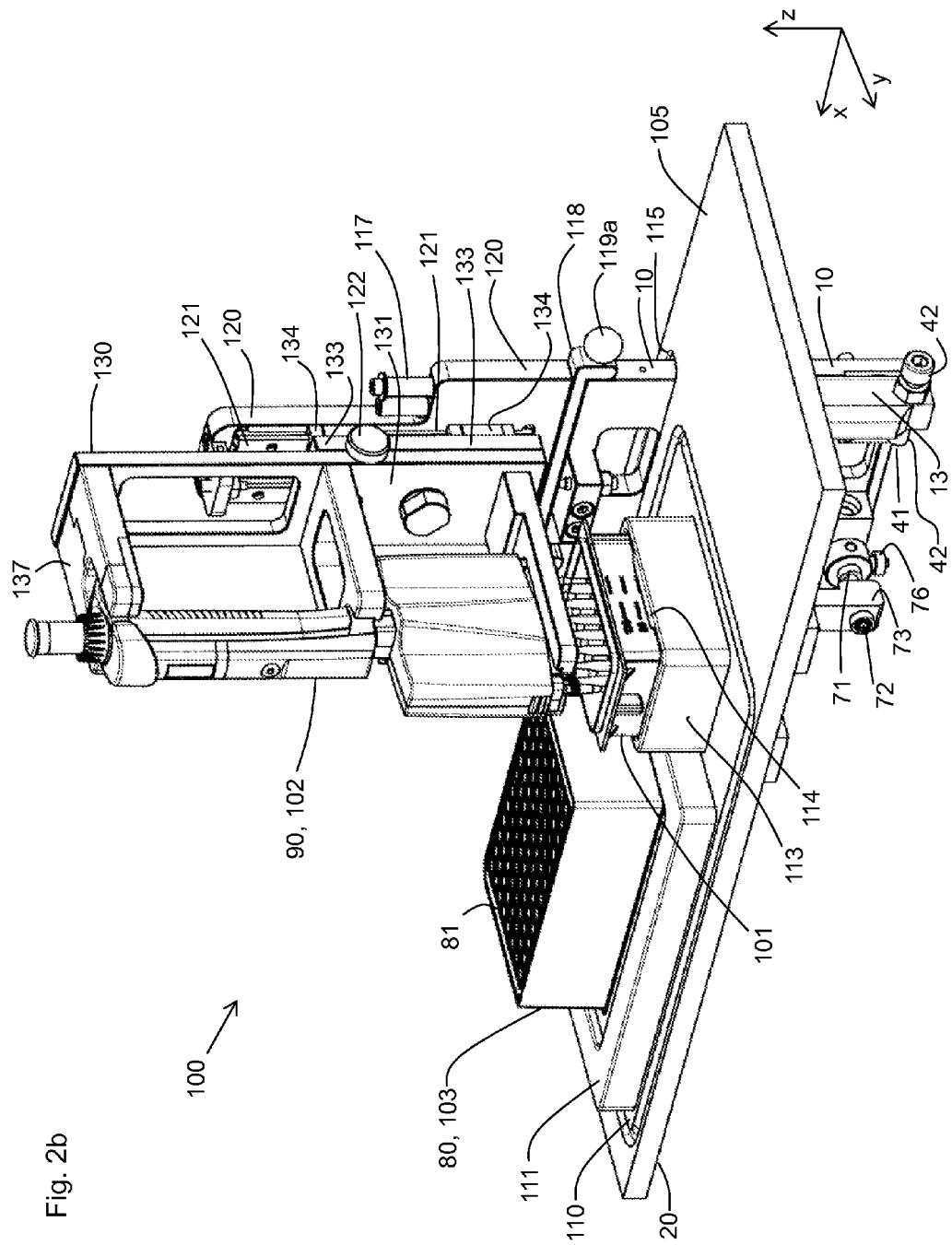
Figure 2C:
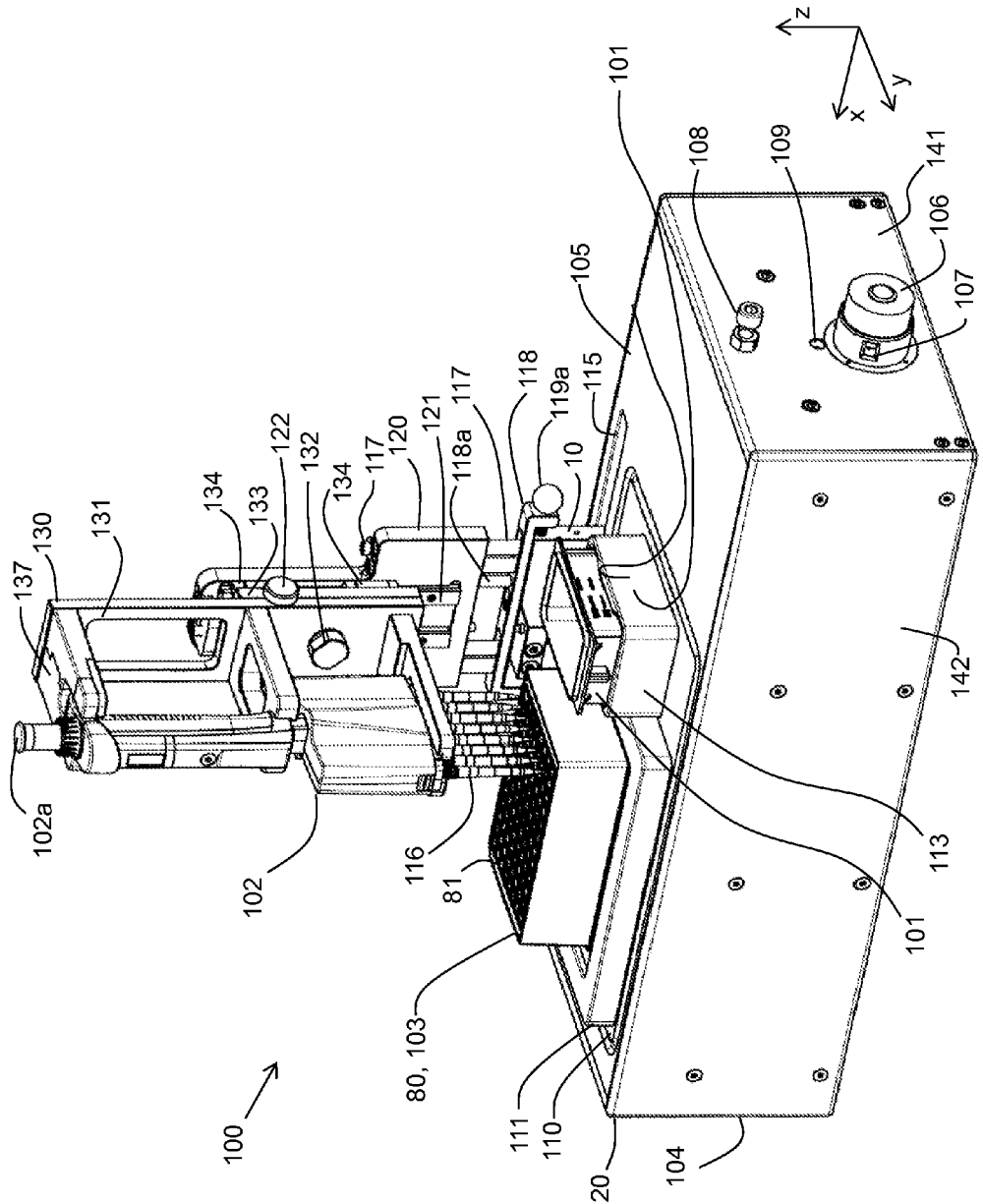
Figure 2D:
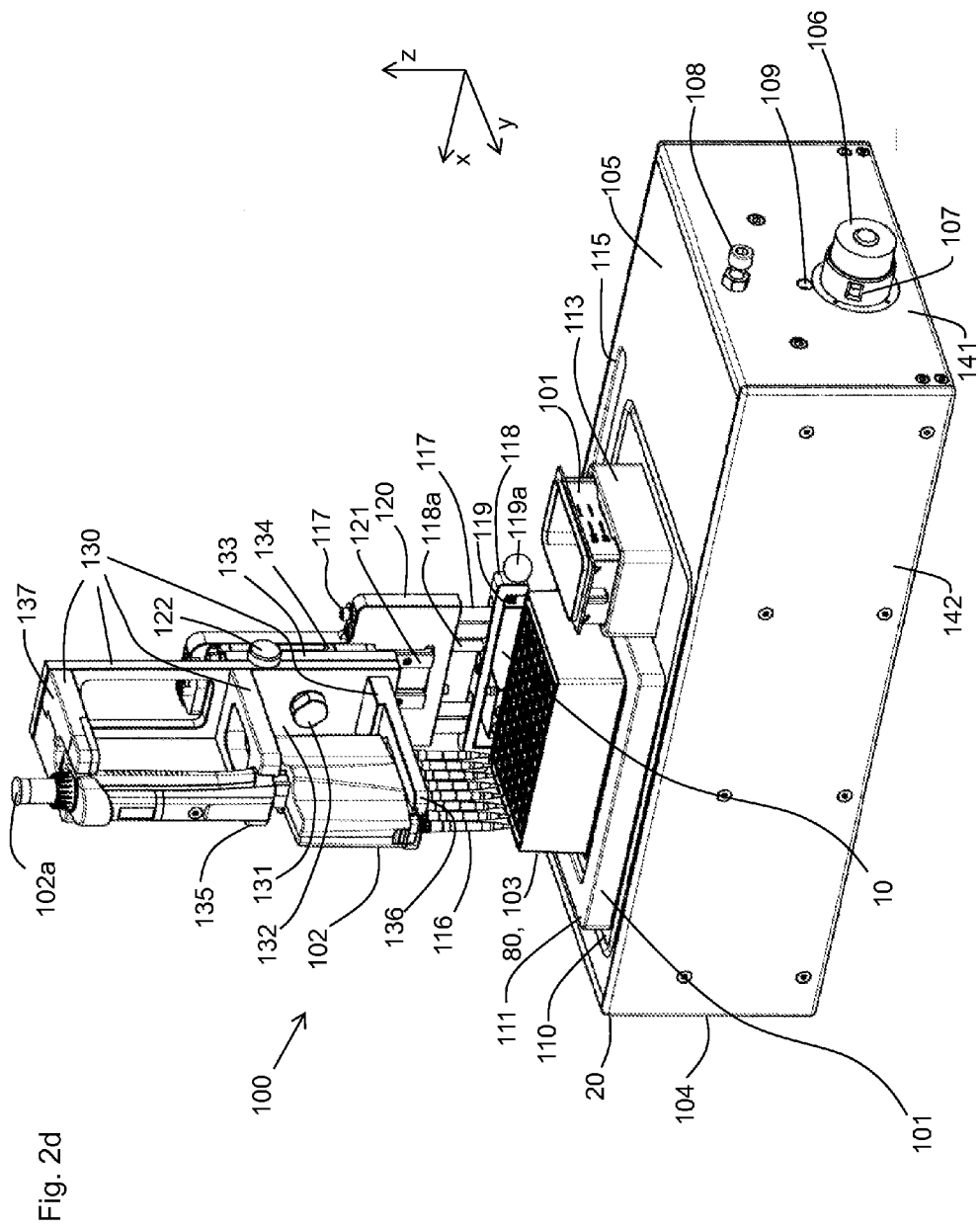
Figure 2E:
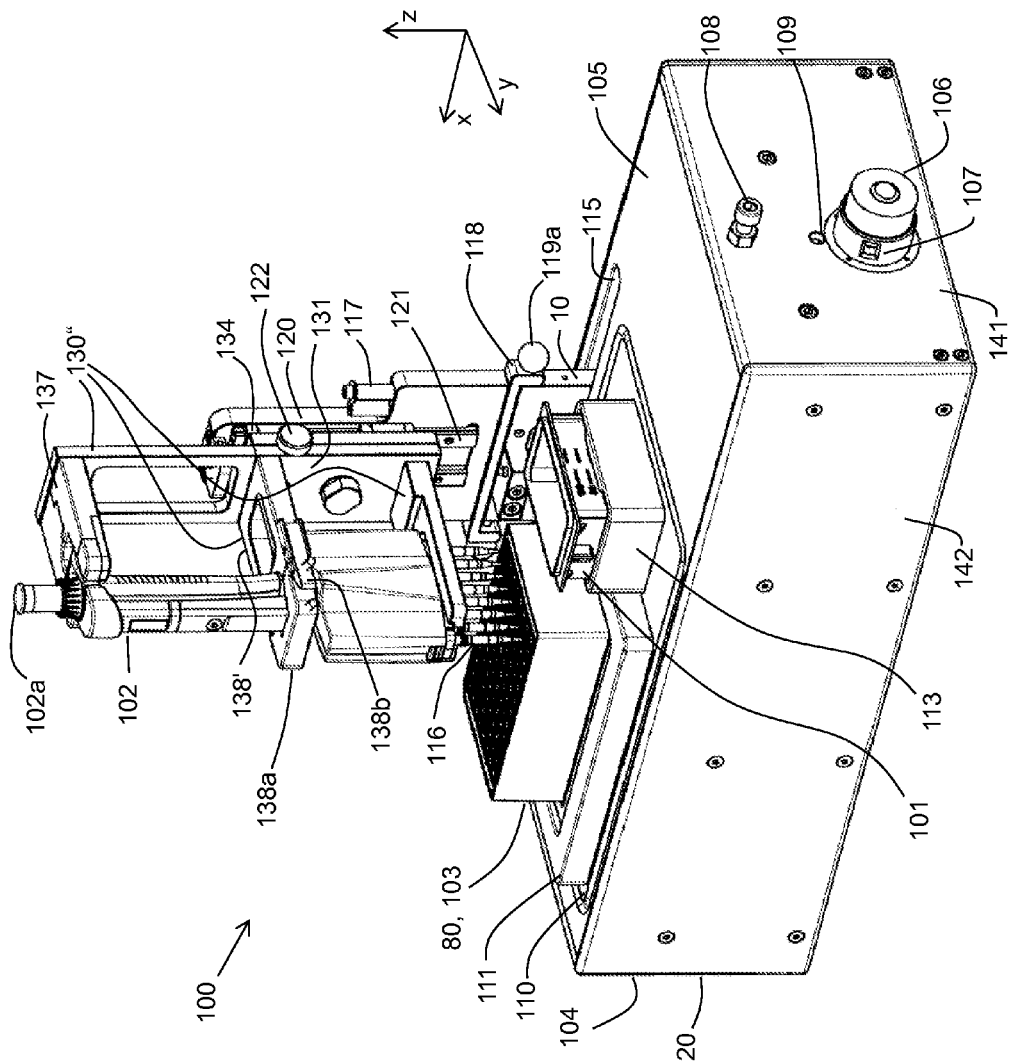
Figure 2F:
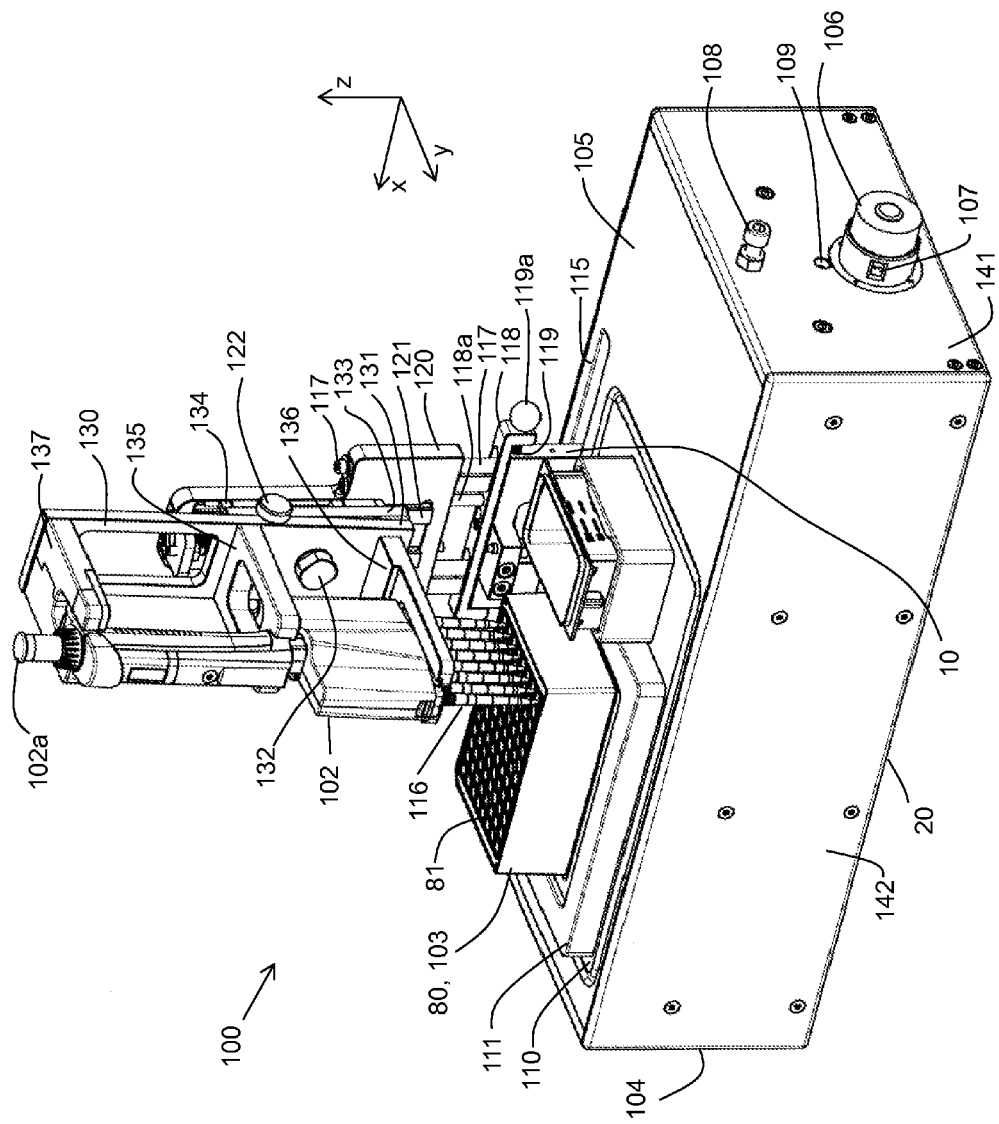

FIGS. 2a, 2b, 2c, 2d, 2e, 2f show perspectively an embodiment of the sample distribution apparatus according to the invention, wherein the first and second part are located in a starting position, wherein the holding device for the sample transport device is lifted to a displacement height (FIG. 2a), is dropped to a sample uptake height (FIG. 2b), is lifted to a displacement height and is arranged above the first row of the well plate in a first target position (FIG. 2c), is arranged above the twelfth row of the well plate in a twelfth target position (FIG. 2d), is arranged in a first target position and is dropped to a sample release height (FIG. 2e) or is arranged in a first target position, is dropped to a sample release height and is arranged inclined (FIG. 2f).

Figure 3B:
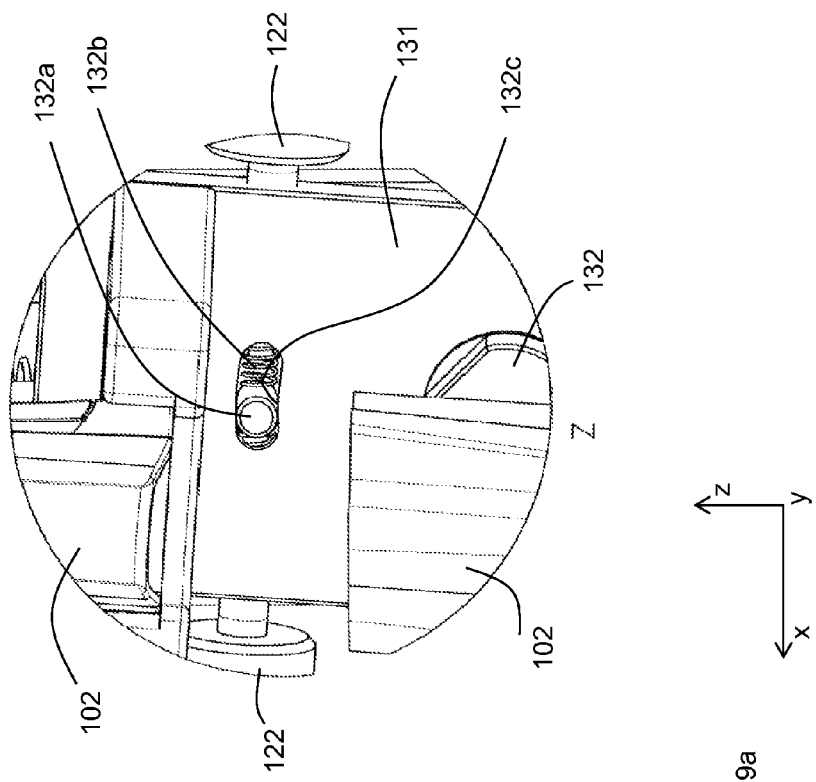
Figure 3A:
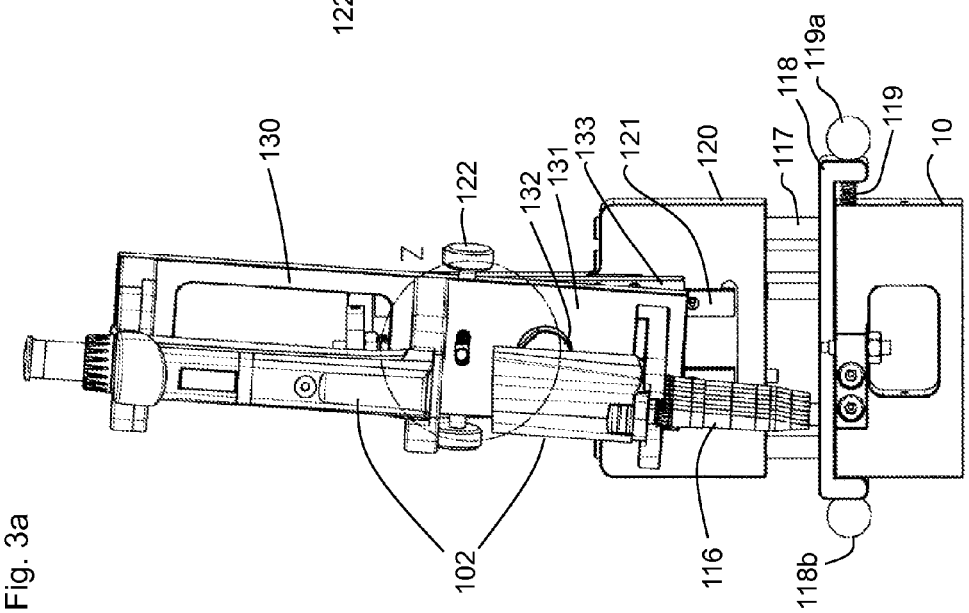

FIG. 3a shows perspectively the holding device for the pipette of the FIG. 2f, at which the holding device is arranged inclined.

FIG. 3b shows a detail of FIG. 3a.

Figure 4A:
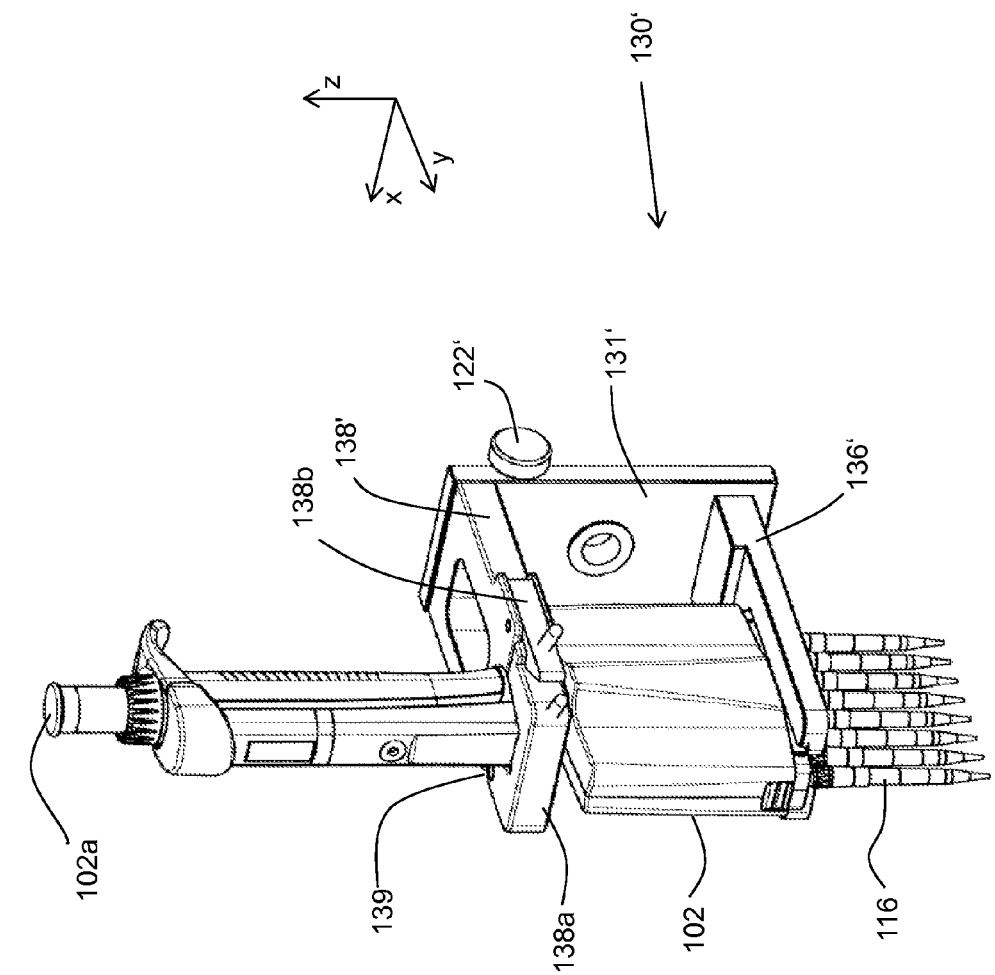

FIG. 4a shows a perspective detail view of a second embodiment of the holding device for a pipette.

Figure 4B:
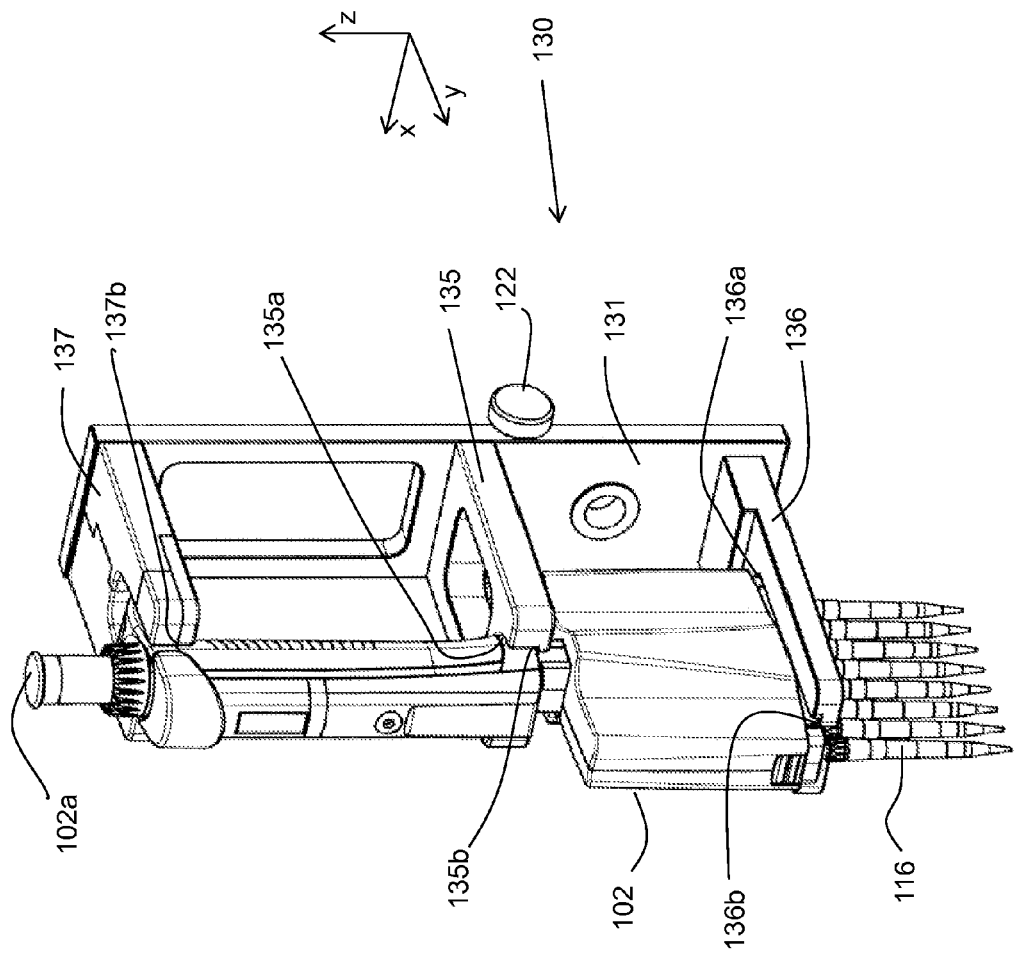

FIG. 4b shows a perspective detail view of the embodiment of the holding device for a pipette according to the embodiment shown in the FIGS. 2a to 2f.

Figure 5A:
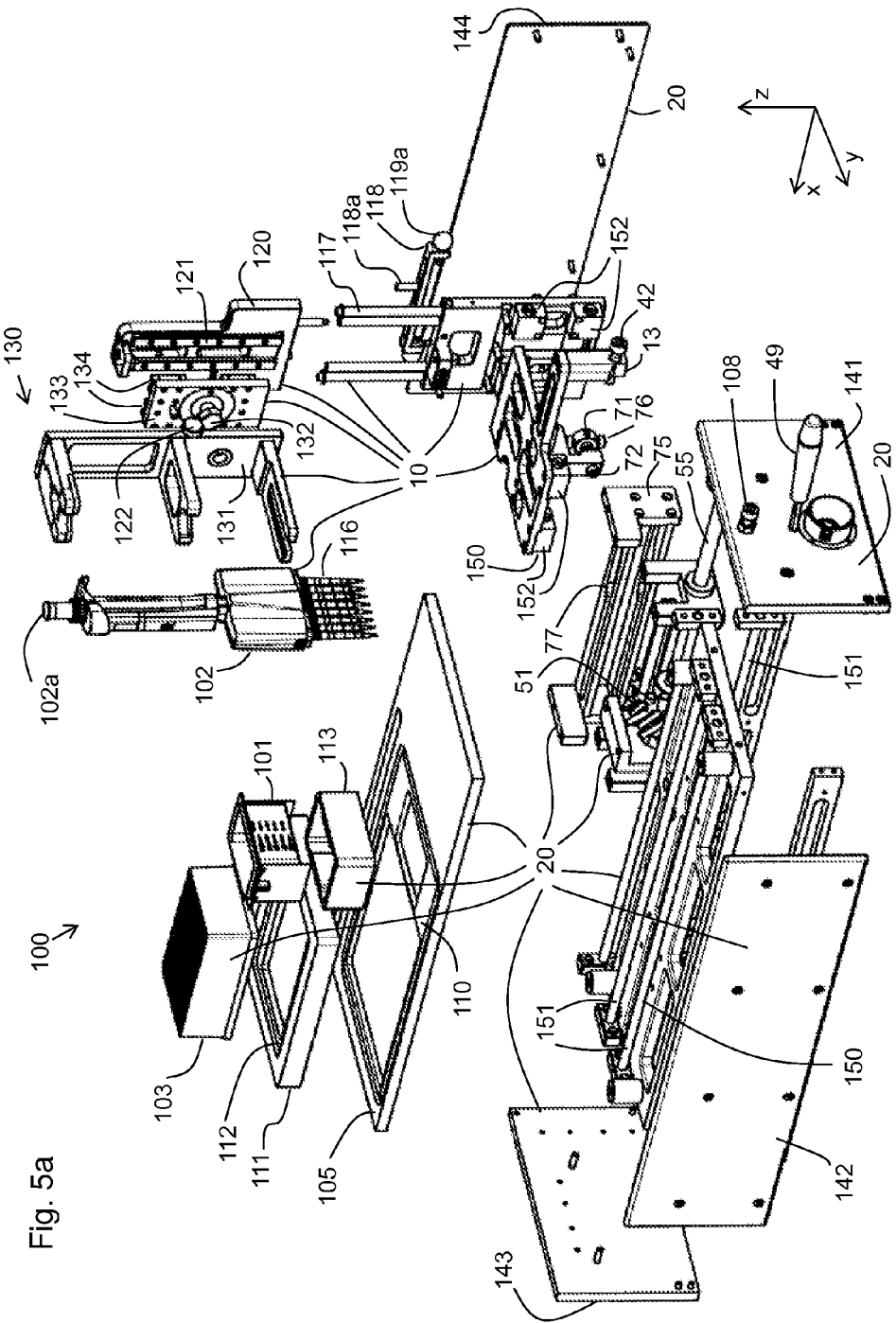
Figure 5B:
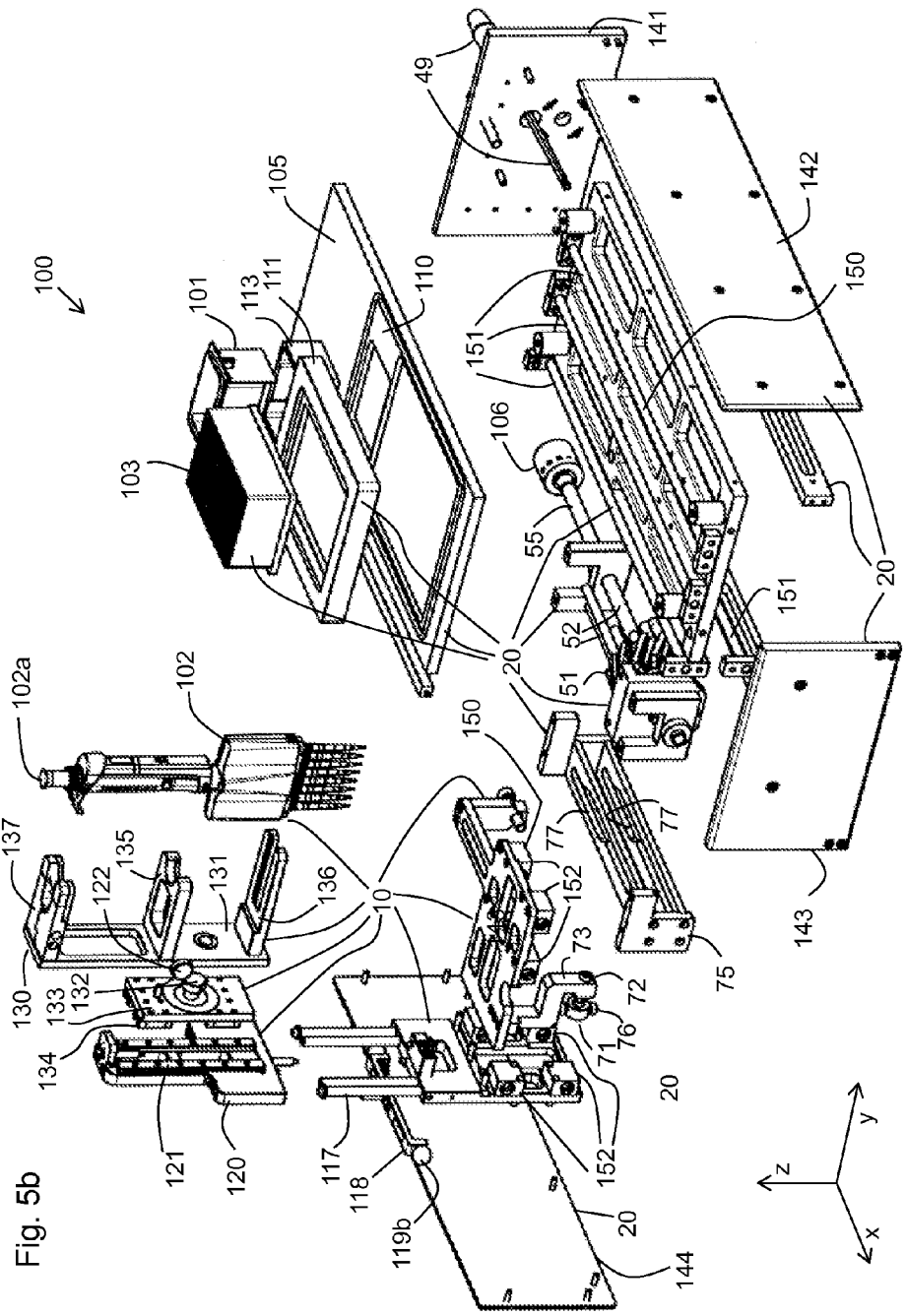

FIGS. 5a and 5b show, respectively perspectively, but from different view angles, an explosive view of the sample distribution apparatus, which is shown in the FIGS. 2a to 2f.

FIG. 6 shows perspectively the embodiment of the positioning device, according to the invention, which is used for the sample distribution apparatus of the FIGS. 2a to 2f, 5a and 5b.

Figure 6A:
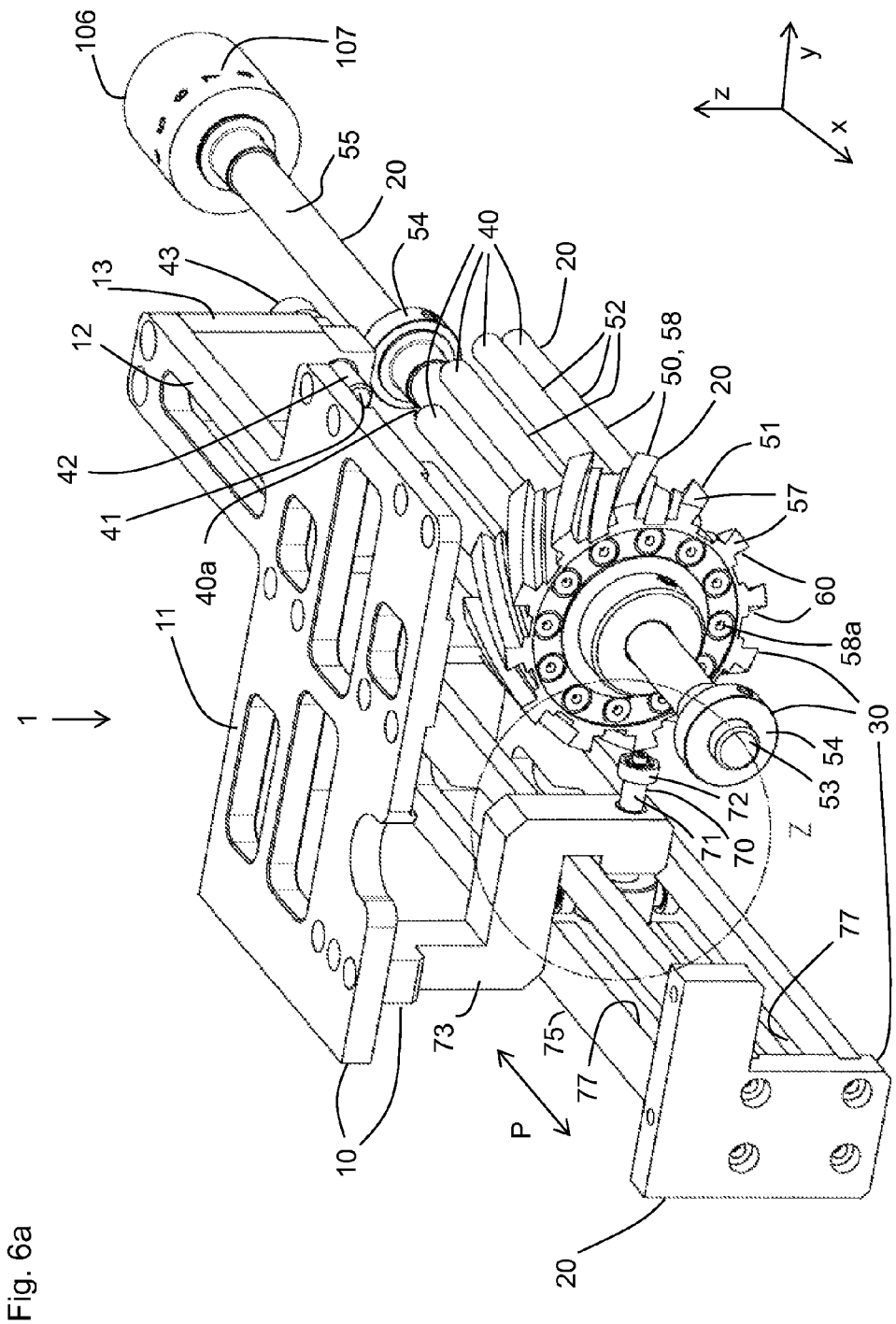
Figure 6B:
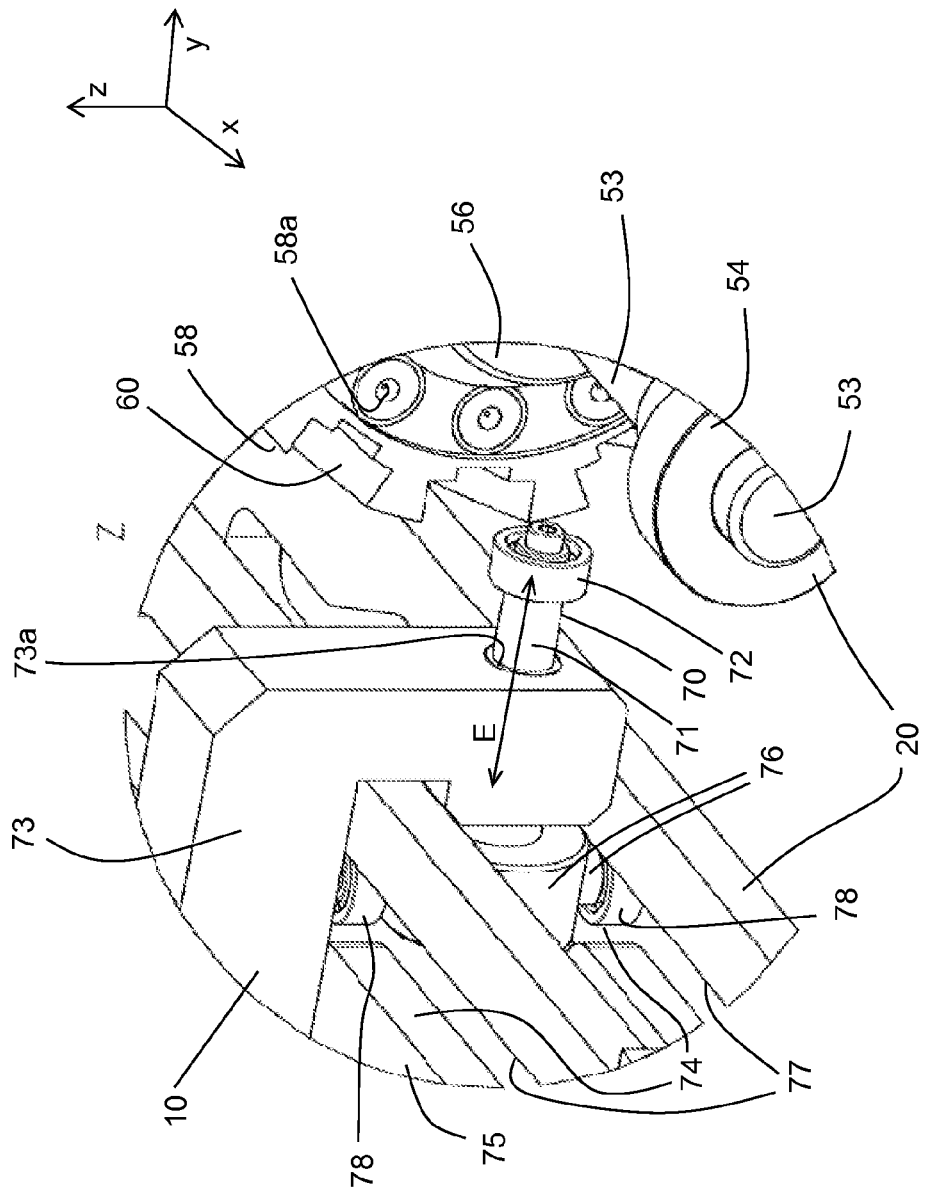

FIG. 6b shows a detail of the positioning auxiliary device 30 from FIG. 6a.

Figure 6C:
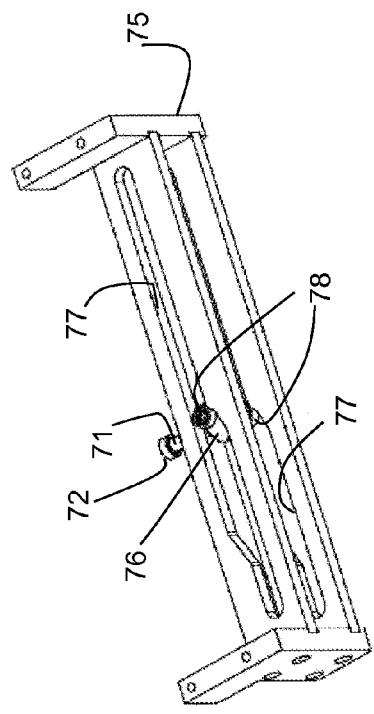

FIG. 6c shows a perspective back view of the slotted link device 75, by which of means the linear positioning motion P effect a position depending engagement and disengagement of the first means for coupling along the direction E in FIG. 6b.

Figure 6D:
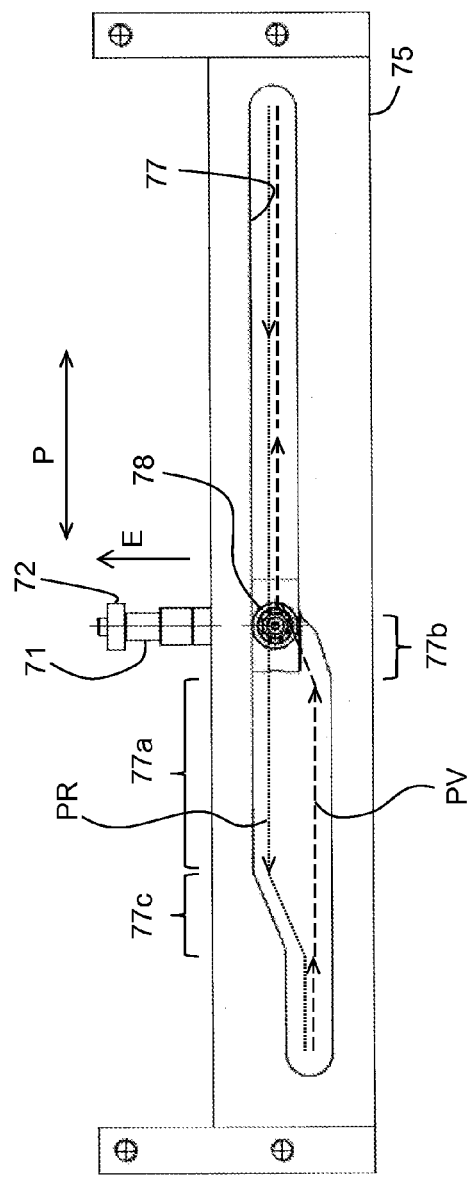

FIG. 6d shows the slotted link 77 of the FIGS. 5a, 5b, and 6c to 6c in a top view.

Figure 7:
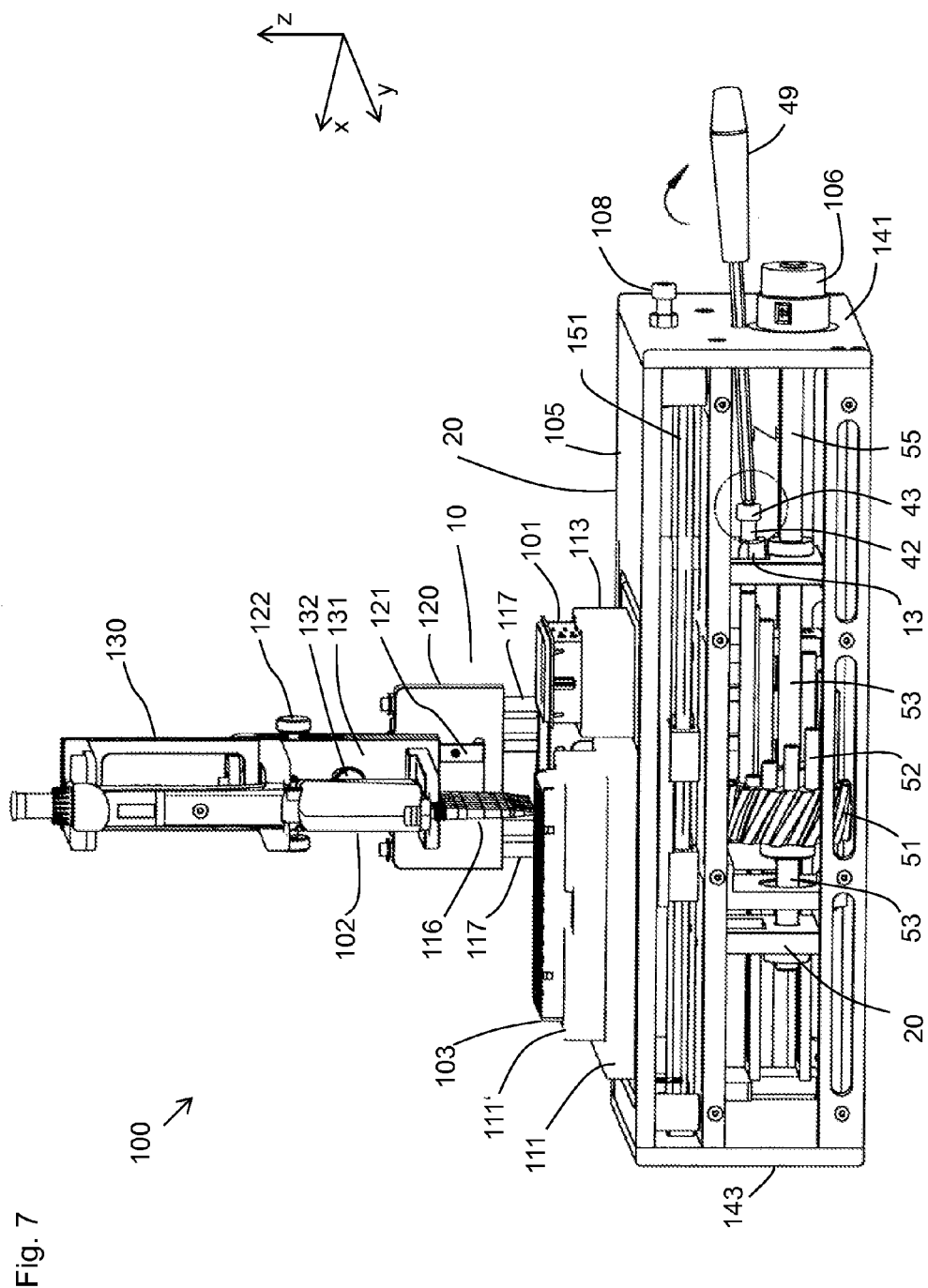

FIG. 7 perspectively and frontal the sample distribution apparatus of the FIGS. 2a to 2f and its means for fine adjusting the target positions of the positioning device, shown in FIG. 6a.

Figure 8B:
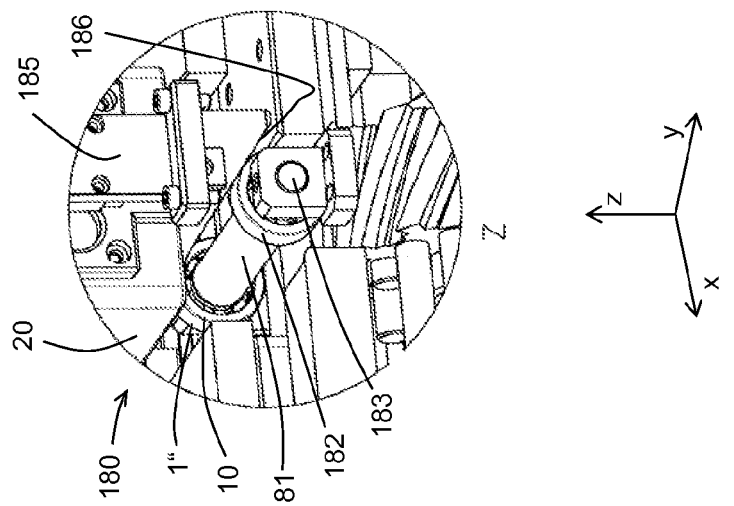
Figure 8A:
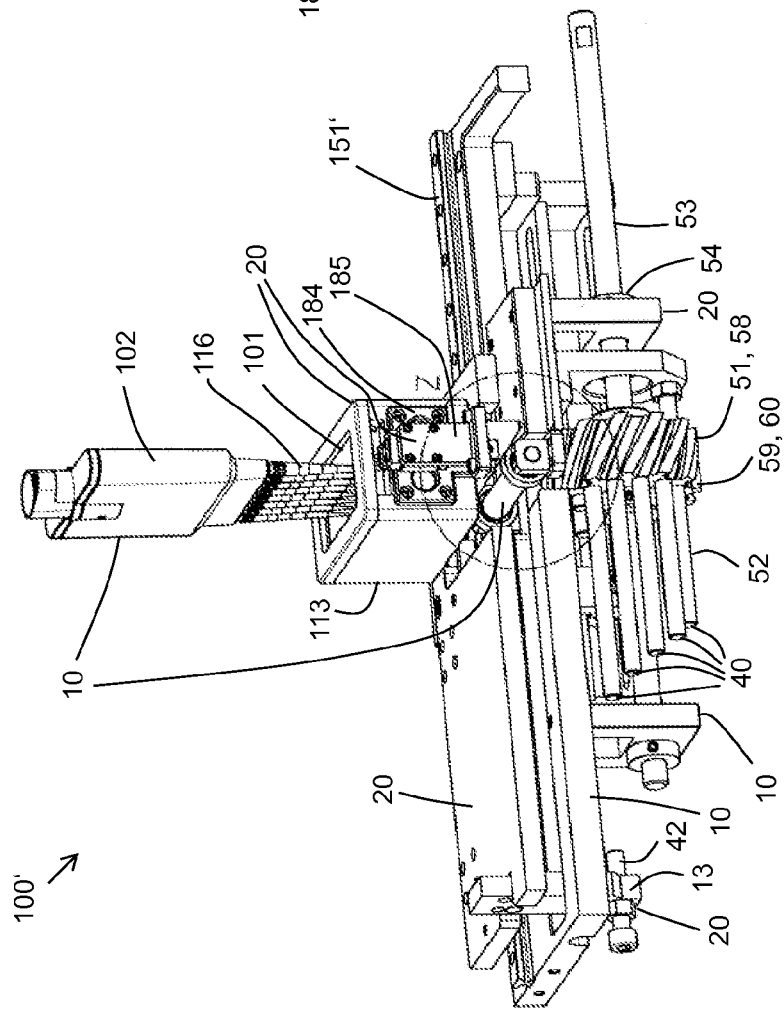

FIG. 8a shows perspectively from behind a detail of a modified sample distribution apparatus according to the invention of FIGS. 2a to 2f, in particular its automatical height adjustment device, which lifts the sample supply container at a starting position for adjusting a uptake height of the holding device by means of the positioning motion.

FIG. 8b shows a detail of the FIG. 8a.

Figure 9:
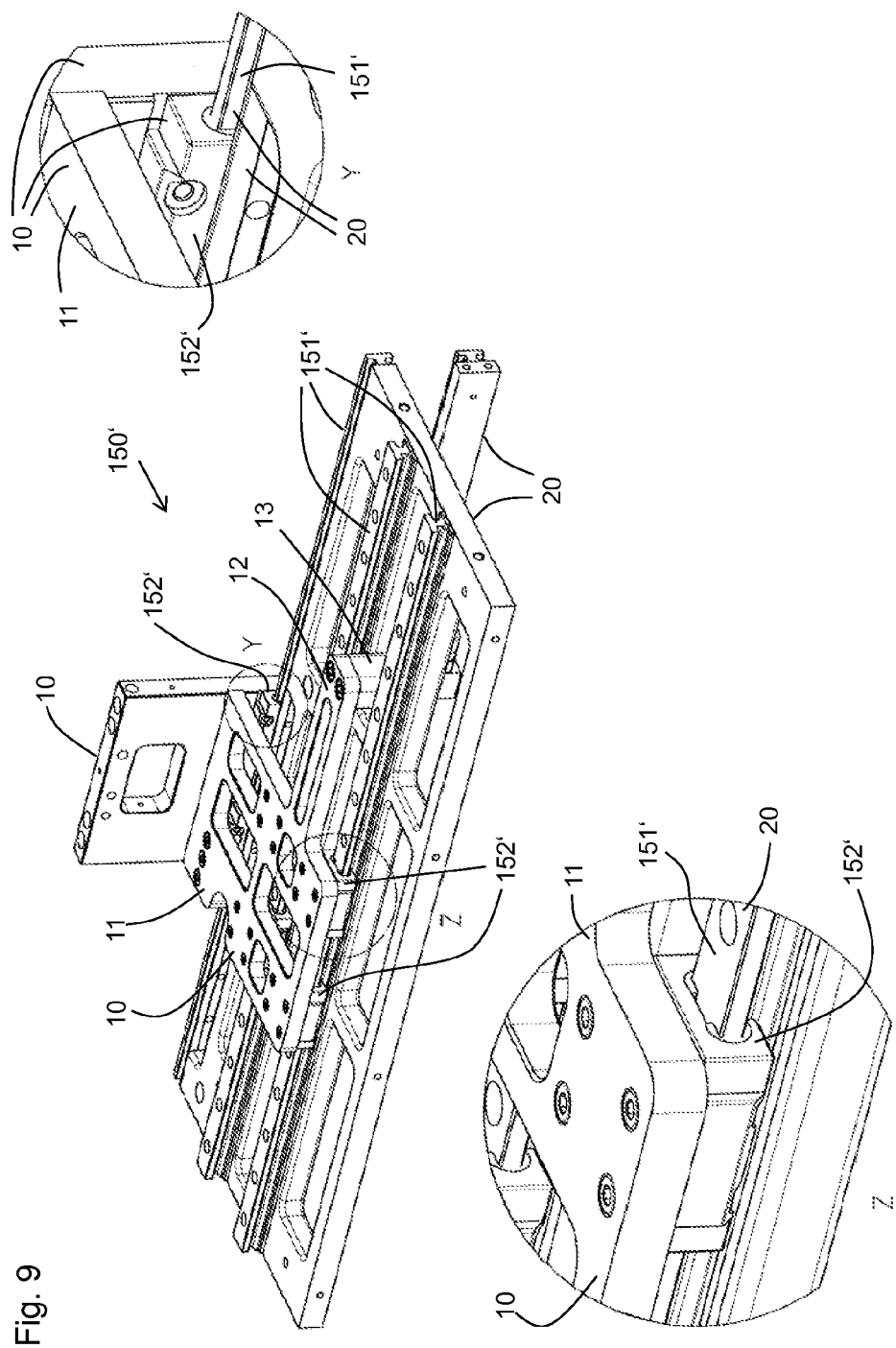

FIG. 9 shows an alternative embodiment of the guiding device compared to the guiding device, which is used the positioning device of the sample distribution apparatus in FIGS. 2a to 2f, with detail views, namely the guiding device from FIG. 8a.

FIGS. 10a and 10b show perspectively from above the holding device with pipette of the sample distribution device in FIGS. 2a to 2f arranged above of their sample holder device, which is equipped with a 384-well plate, in an 0°-arrangement of the well plate and in 180°-arrangement of the well plate.

FIGS. 11a to 15b show six different embodiments of adapter elements of the sample holder device of the sample distribution apparatus of FIGS. 2a to 2f, for six different sample holder embodiments, namely in perspectively isometric view (FIGS. 11a, 12a, 13a, 14a, 15a) or in perspective explosive view (FIGS. 11b, 12b, 13b, 14b, 15b).

Figure 16A:
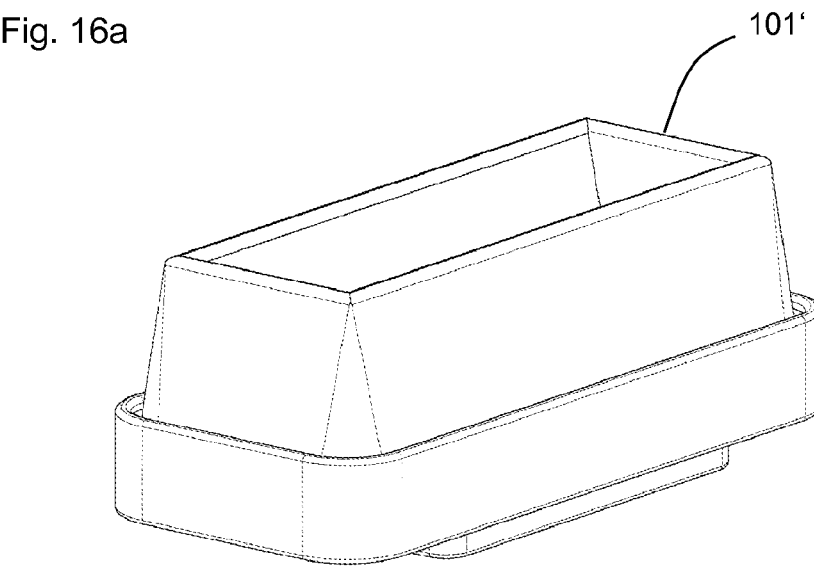

FIG. 16a shows an embodiment of a sample supply container, which can be used with the sample distribution apparatus of the FIGS. 2a to 2f.

Figure 16B:
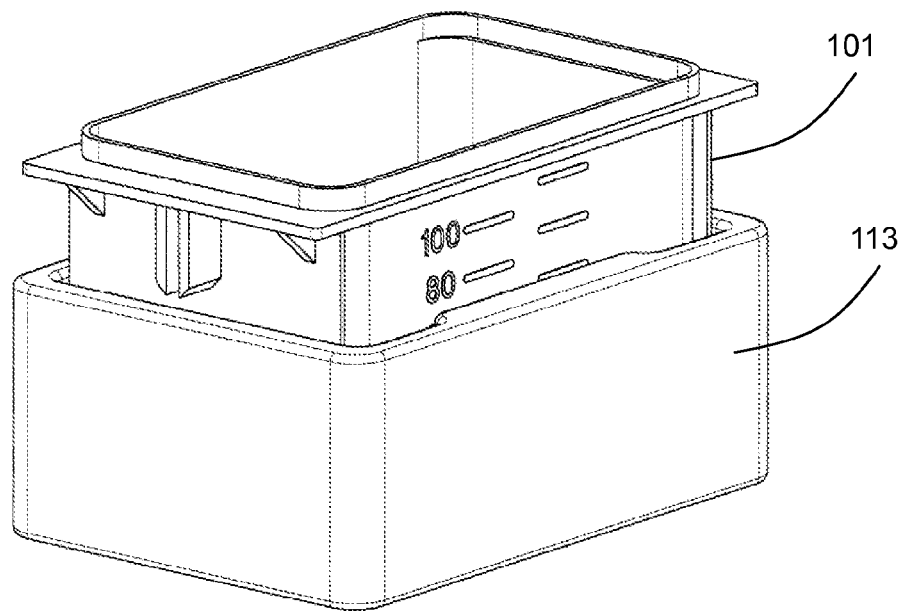

FIG. 16b shows the sample supply container shown in FIGS. 2a to 2f.

Figure 17:
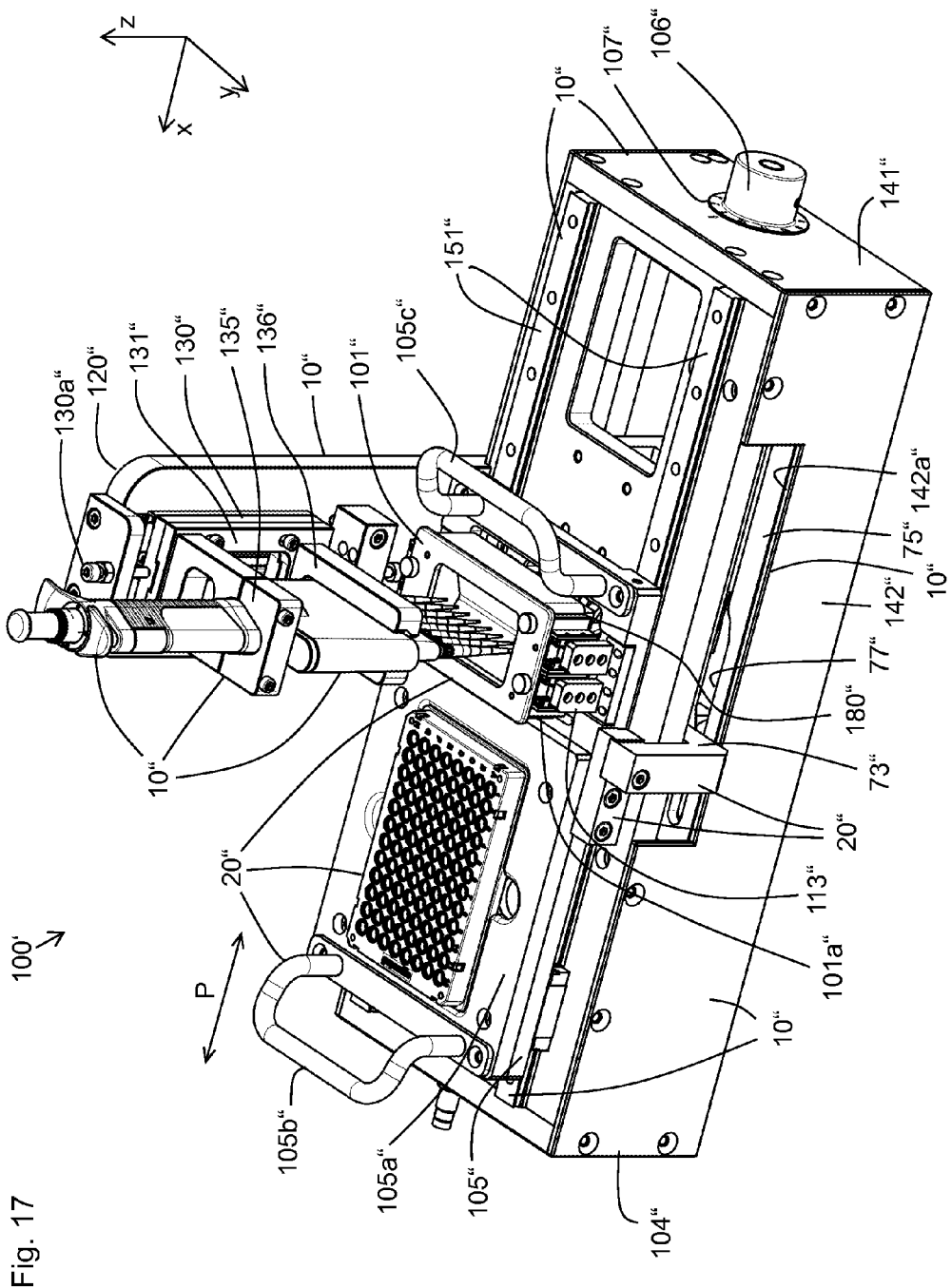
Figure 18:
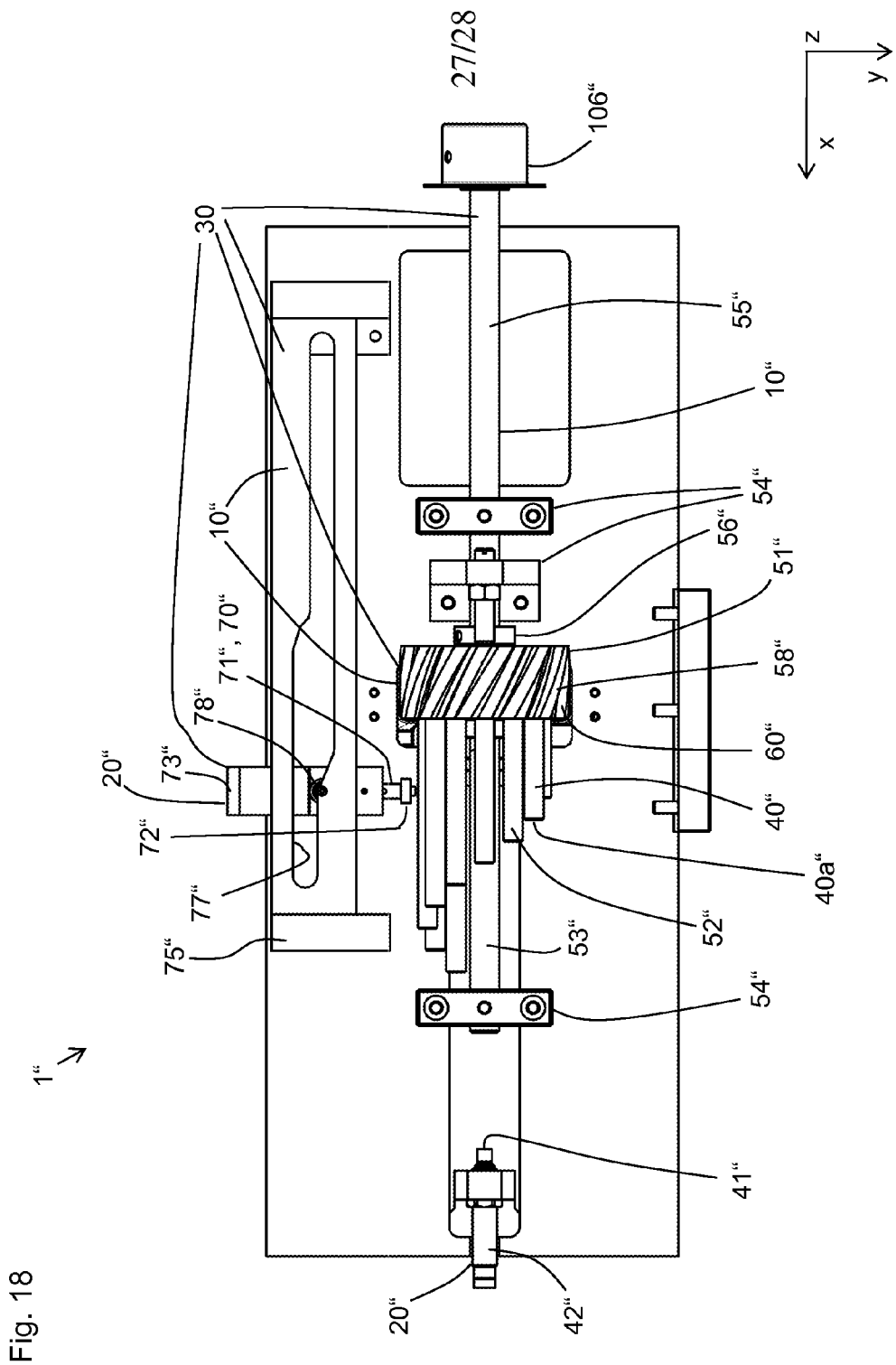
Figure 19:
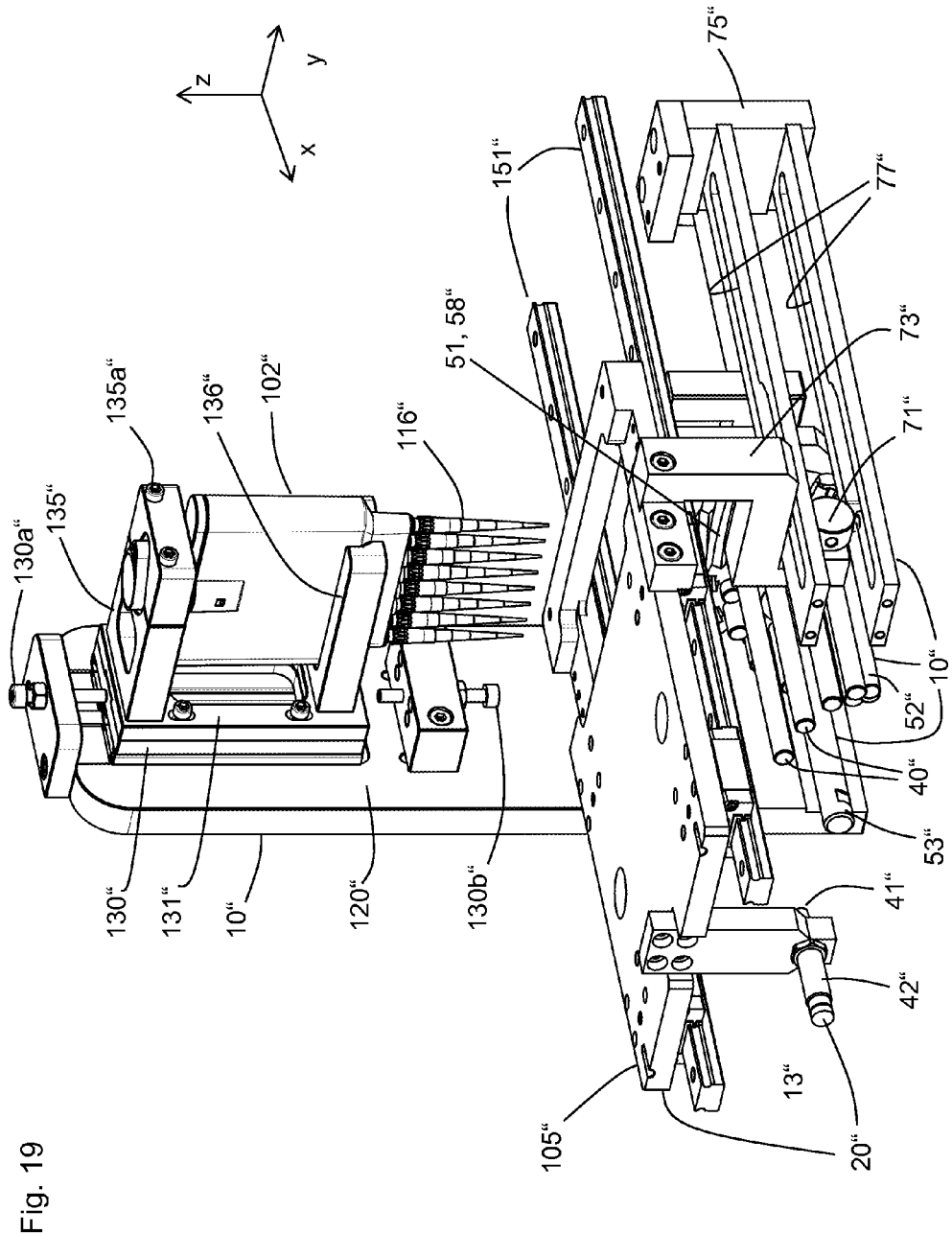

FIGS. 17 to 19 show a second embodiment of the sample distribution apparatus according to the invention with a positioning device according to the invention in another embodiment, which features a second part, which is moveable against the stationary housing and a substantially unmovable first part.

FIG. 1 shows a first embodiment of the positioning device 1' according to the invention. The latter is suitable to be used with a sample distribution apparatus, for example the sample distribution apparatus of the FIGS. 2a to 2f, thus, for example, in pipetting apparatus, at which a liquid sample, for example a solution with PCR-reagents, is distributed from a sample supply container by means of a multi-channel pipette to the sample wells of a well plate. The positioning device 1' is configured such that the first part 10' is moveable relative to the second part 20' in a lateral direction R (denoted by the double arrow) of motion. At the first part 10' a sample transport device 90' is arrangeable, for example a multi-channel pipette, and at the second part 20' a sample holder 80' is arrangeable, for example, a well plate with 96 (or, for example, also 384) sample wells 81'. The positioning device 1' is configured such that a positioning motion of the first and second part relative to each other between a starting position, which corresponds to the position of the first part drawn dashed in FIG. 1, and an adjusted target position can be performed. A starting position offers the possibility in the embodiment at hand that in the starting position a sample can be taken up into the sample transport device 90', for example by aspirating in the pipette tips of a pipette. A target position, here, provides the possibility that in said target position the sample is releasable from the sample transport device to the sample holder. In FIG. 1 the first and second part are located in the seventh target position of totally twelve possible target positions, which can correspond to the sample release positions of the first part to the first to twelfth row of a 96-well plate, respectively.

The positioning device 1' offers the advantage that no additional user activity is required to change the adjusted target position, because the change of the target position occurs automatically by the obligatory positioning motion. This is achieved by means of a positioning auxiliary device 30', which provides the means for limiting 40' the relative motion of the first and second part in the adjusted target position, which further provides means for adjusting 50' the n-th target position from a plurality of N=12 predetermined target positions as the adjusted target position, which further provides means for changing 60' the adjusted target position from the n-th target position to a (n+1)-th target position, and which further provides first means for coupling 70' of said positioning motion and said means for changing, such that the change from said n-th target position p7 to said (n+1)-th target position p8 can be effected by means of the first means for coupling during a lateral positioning motion.

The means for limiting 40', schematically shown, contains a stopping area 40', which is arranged at the means for adjusting 50'. In the seventh target position shown, a counter stopping portion 40a' of the first part 10' contacts at the stopping portion 40', which is arranged at a subcomponent 52' of the means for adjusting 50'. The subcomponent 52' is (releasable) fixed at the second part via the locking element 51', which is mounted at the second part, of the means for adjusting 50'. By the attachment it is in particular possible that in the case of a manual performance of the positioning motion by the user the target position can be easily approached, because the lateral positioning motion is blocked at the seventh target position. For the positioning device 1' it is provided that during the lateral positioning motion, that is either on the way from the starting position to the n-th, for example, the seventh, target position (first alternative embodiment), or on the way back from the same to the starting position (second alternative embodiment) a projection element 11', which is arranged at the first part 10', actuates the first means for coupling 70', which actuates the means for changing 60'. Said means for changing 60' can provide, for example, a locking device 60', which temporarily lifts the subcomponent 52', such that underlying locking cam 52a' is lifted from the locking recess of the locking element 51', which allows further sliding of the locking cam 52a' to the (n+1)-th, for example, the eights locking recess, where the locking cam 52a' engages again and fixes the target position n+1.

FIG. 2 to FIG. 16b show an embodiment of the sample distribution apparatus 100 according to the invention, which provides a positioning device 1 (referred to in FIG. 6a) according to a second embodiment of the invention, as well as different subcomponents of the sample distribution apparatus and suitable accessories in preferred embodiments.

FIGS. 2a, 2b, 2c, 2d, 2e, 2f show perspectively an embodiment of a sample distribution apparatus 100 according to the invention, wherein the first and second part are located in a starting position (FIGS. 2a, 2b) and wherein the holding device for the sample transport device is lifted to a displacement height (FIG. 2a) or dropped to a sample uptake height, respectively (FIG. 2b), when the holding device is lifted to a displacement height and is arranged above the first row of the well plate in a first target position (FIG. 2c) or above the twelfth row of the well plate in a twelfth target position, respectively (FIG. 2d), wherein the holding device is arranged in a first target position and is dropped to a sample release height (FIG. 2e), or is arranged in a first target position, dropped to a sample release height and arranged inclined (FIG. 2f).

The sample distribution apparatus 100 is a pipetting apparatus for use in a research laboratory, for example, by means of which the manual distribution of a sample by pipetting from a sample supply container 101 by means of a sample transport device 90, in particular the multi-channel pipette 102, to a sample holder 80, in particular the well plate 103, is facilitated for a user. The pipetting apparatus is configured for pipetting of 96 and 384 well plates, by providing N=12 target positions, in particular, wherein the fixed distance of the target positions in an x-direction corresponds to the distances of the 12 rows of the well plate 103 in the x-direction. Said distance is the standard distance of well plates with 96 sample wells. The pipette shown is a production model of type "Mehrkanalpipette Eppendorf Research® plus" of the Eppendorf AG, as it is sold in year 2009 by the Eppendorf AG, Hamburg, Germany. It provides a manual actuation button 102a, which effects the release of the sample contained in the pipette tips 116 upon pushing down the button in a vertical direction, conveying the sample in this way to the sample wells 81 of the well plate 103. FIGS. 2a to 18 are isometric or true scale views of the preferred embodiments of the invention. Therefore, preferred dimensions or relations to dimensions of the components according to the invention can, preferably, be taken from the Figures or at least estimated from the Figures.

The pipetting apparatus 100 provides a housing 104 with an upper cover plate 105, below which the positioning device 1 is largely arranged such that a contamination of the positioning device by sample liquid is prevented. An adjustment wheel 106 is arranged at the right side panel of the housing such that a user can quickly adjust a desired target position of the first and second part by turning the wheel. With the aid of means for marking of the adjusted target position 107, the adjusted target position can be directly recognized or adjusted by the user. The marking is also valid during the automatic change of the target position from n to n+1. Further, a means for adjustment, namely the adjustment screw 108, of the height of the supply container holder (not visible) is provided, by means of which the height of the supply container can also be adjusted manually. The side panel, moreover, provides an opening 109, by means of which a tool can be inserted into the housing 104. By means of the tool, a means for fine adjustment of the position of the counter stopping area can be adjusted, namely a hexagon key for the adjustment of a hexagon screw nut wheel, which is described later with reference to FIG. 7.

The cover plate 105 is configured such that a sample holder 90 and a supply container 101 can be fixed at the cover plate 105 at least in the x-y-plane. The cover plate provides a recessed holding plate with a trough section 110, in which a first collet is provided for the uptake of an adapter frame 111, which is mounted by form closure to said collet by the form-closure engagement of holding projections or a circumferential holding border, arranged below, and which is fixated in the x-y-plane, in particular. Within the adapter frame 111, a circumferential recess 112 is provided, in which the lower border of the well plate 103 engages, the well frame being from type "Eppendorf Deepwell Plate®" of the Eppendorf AG, Germany, with 96 samples wells 81, which are circular in a cross section, and periodically arranged in 12 rows and 8 columns in the x-y-plane. This way, the well plate 103 is fixated to the x-y-plane at the housing, in particular.

Further, a second collet is provided in the trough section 110 of the cover plate 105, at which is provided a holding frame 113 for holding a sample supply container 101, which is also fixated to said second collet by means of a form-closures engagement. Further, the holding frame of the supply container is configured to guide the sample container during a height adjustment, by having provided its inner side with means 114 for guiding the sample container.

The cover plate 105 moreover provides, running in x-direction, a third, slit-shaped opening 115, wherein the first part 10 can be manually moved along said opening, while being fixated in y- and z-direction. Said motion is said positioning motion, by means of which a user drives part 10 from an uptake position, in which the liquid sample is aspirated by pipetting into the pipette tips 116 of the multi-channel pipette 102, as for example shown in FIG. 2a, into a target position, shown for example in FIGS. 2c, 2d, in which the liquid is released from the pipette tips to the subjacent sample wells after lowering into a release position (FIG. 2e) by a manual actuation of the pipette 102.

Further details for the preferred configuration of said cover plate 105 can be derived from the FIGS. 16a and 16b. Alternative embodiments of the cover plate for taking up other adapter plates and appropriate sample holder are shown in the FIGS. 11a, 11b, 12a, 12b, 13a, 13b, 14a, 14b and 15a, 15b. Preferably, sealing means, for example rubber sealings, are provided to prevent said sample material, which may have unintentionally arrived in the area of the sample holder collet and the supply container holder, in particular into said trough area, advances into the inside of the housing.

At the first part 10 a first height adjustment device is provided to which the guiding struts 117 are assigned to, the latter being connected to the first part 10 (see FIG. 3a). The guiding struts 117 assigned to the first part engages into guiding openings form-closed and moveable, which are provided at the bottom side of the vertical member and extends from their upwards in the vertical member. By means of a fixating element 118 at a first part 10, at which the distance pin 119 is spring mounted and horizontally moveable, the vertical member 120 can be fixated in a predetermined position with respect to the first part 10 in z-direction. The fixating element provides a distance element 118a extending upward, on which rests the vertical member 120 with the pipette 102 in a positioning position such that the first part with the pipette 102 can be moved away over the microwell plate 103. For releasing of a sample from the pipette 102 into the sample wells of the well plate 103, the fixating element 118 is pulled to the left by means of a button 118b such that the distance element 118a becomes arranged below a recess (not shown) in the vertical member 120 when the distance element becomes completely countersunk, if the vertical member is shifted downwards in relation of the first part 10 as long as the bottom side of the vertical member rests on the fixating part 118. In this defined lower position the pipette tips are located in a release position above or within the openings of the respective sample wells of the well plate 103 such that the sample can be safely and completely released into the predetermined sample well. The height adjustment device can also be configured for the adjustment of more than two heights. Therefore, the user only has to set the height adjustment device to the predetermined, lower position, in particular at the sample release, without having to take care, mandatory, about the height adjustment each time if a new well plate is filled. The height adjustment device further provides spring means for cushioning the motion in z-direction, namely respectively one spring for cushioning the motion of the third part into upward or downward direction, to prevent impacts upon arriving at the end positions.

The vertical member 120 provides a second height adjustment device, to which the rail device 121 and the fixating element 118 are assigned to, as well as the guiding elements 134, which are arranged complementary to the guiding elements 134 at the backside of the intermediate plate 133 of the holding device 130. The second height adjustment device allows, in particular, to further adapt the predetermined heights, to account for varying pipette tip lengths, in particular, if using pipette tips of 10 μl, 100 μl or 300 μl volume (multi-channel base portion).

Further, the vertical member 120 provides an inclination device, to which the inclination axis 132 is assigned to, and by means of which the post plate 131 of the holding device 130 for holding of the multi-channel pipette is pivotable arranged at the intermediate plate 133, such that it can be fixated in pivoted or vertical direction. The inclination device further provides means for an automatic returning 132a, 132b, by means of which the post plate 131, which is inclined within the x-z-plane with respect to the z-axis, can be returned from the inclined position back into the vertical position. Said means comprise the pin 132a, which is firmly attached at the intermediate plate 133 and extends from their forward (in y-direction) and which engages a guiding recess 132c of the post plate 131. The means for the automatic returning further comprise the spring 132b, which is spanned between the pin 132a and the post plate 131 such that an inclination of the post plate 131 against the intermediate plate 132 spans the spring, which automatically causes a restoring force, which urges the post plate 131 back into the vertical position. By means of said inclination device, samples can be released to the inner wall of the sample wells 81 of the sample plate 80, in particular, as described before. The automatical returning allows a controlled inclining of the post plate 131, which facilitates the positioning of the pipette tips 116 into the desired release position.

The holding device 130 for holding the multi-channel pipette 102 is shown more in detail in FIG. 4b, substantially, and an alternative embodiment of the holding device 130' is shown in FIG. 4a.

In FIG. 2b, the holding device 130, 131, 135, 136, 137 (third part) is dislocated far downward into an uptake height, to aspirate samples into the pipette tips 116 For said purpose, the first height adjustment device, to which the guiding struts 117 are assigned to, as well as the second height adjustment device, to which the guiding rails 121 and the guiding elements 134 are assigned to, are dislocated into the lowest position. FIG. 2e provides the alternative holding device 130" with different middle bearing 138', which is further explained with reference to FIG. 4a.

FIG. 3a is a perspective side view of the holding device 130 for the pipette of FIG. 2f, wherein the holding device 130 is arranged inclined. A middle part of the multi-channel pipette 102 is not shown in said figure, to allow the view on the detail shown in FIG. 3b. FIG. 3b shows a detail of FIG. 3a, namely the fixating mechanism of the height adjustment with the fixating element 122.

FIG. 4b shows a perspective view of a detail of the embodiment of the holding device 130 for a pipette 102, which is shown in the FIGS. 2a to 2f. The holding device 130 provides the post plate 131, at whose front side an upper bearing element 137, a middle bearing element 135 and a lower bearing element 136 are mounted and extend forward horizontally from the front side of the post plate 131. Each bearing element provides a substantially U-shaped accommodation recess 135a, 136a and 137a, which are configured for the substantially form-closed accommodation of the pipette 102, with the aim to safely hold it during the positioning and pipetting process. For said purpose, the accommodations 135a, 136a and 137a provide a bearing section 135b, 136b, 137b, which can be arranged, in particular, at the lower area of the inner side of the respective accommodation. At the upper side of the bearing section, a downward facing section of the pipette 102 may rest, respectively, and in fact rests preferably, but, however, does not have to rest in each case. It is also possible and preferred that only one bearing section for holding the pipette is provided.

FIG. 4a shows a perspective view of a detail of a second embodiment of the holding device 130' for a pipette. The holding device 130' provides two bearing elements 138' and 136'. In contrast to the holding device 130, the holding device 130' does not provide an upper bearing element, which is arranged at the height of the actuation button of the pipette. Instead, the bearing element 138' provides a locking device 138a, 138b, which provides a locking clamp 138a and an engaging pawl 138b, which is pivotable around a rotation axis, wherein the engaging pawl 138b is pressed into the locking position by means of a spring not visible, wherein the clamp 138a is secured in the locking position shown and a dropping of the pipette is prevented. In the locked state shown, an engaging projection of the pawl engages a complementary engaging recess at the locking clamp. For opening the locking device, the user pulls the engaging pawl away from the locking position to the right and pivots the locking clamp around the rotation axis 139 to the fore. It is possible to also provide the holding device 130 with such a locking device.

FIGS. 5a and 5b show, respectively, but from different view angles, a perspective exploded view of the sample distribution apparatus, which is shown in the FIGS. 2a to 2f. In particular, it is shown: the right side panel 141 of the housing 104, the left side panel 143, the front side panel 142 and the backside panel 144, components of the first part 10 and of the second part 20 of the positioning device 1, in particular the means for adjusting 51, 52, further, a guiding device for guiding the first part 10 at the stationary second part 20 in a linear positioning motion along the x-axis. The guiding device 150 further provides guiding struts 151, which are firmly connected to the second part 20, further, guided bearing elements 152, which are firmly arranged at the first part 10. Each guiding strut guides two bearing elements of the first part, which are arranged in distance, whereby the first part is guided stable along the guiding direction. A guiding strut engages the opening of a bearing component form-closed, respectively. The play of the guiding strut in the guiding opening is configured for a possibly frictionless sliding of the guiding elements at the guiding strut. A bearing element can comprise anti-friction bearings, ball-bearings, or floating bearings, to achieve a possibly frictionless and low-wear guiding.

FIG. 6a shows perspectively the embodiment of the positioning device 1 according to the invention with the positioning auxiliary device 30, which is used in the sample distribution apparatus of the FIGS. 2a to 2f, 5a and 5b. FIG. 6b shows a detail of FIG. 6a, as well as FIGS. 6c and 6d. The positioning device 1 provides the first part 10 and the second part 20, wherein the positioning device is configured such that a positioning motion of the first and the second part relative to each other between a first position, namely a starting position, at which in the sample transport device is lowered into a uptake position, and an adjusted target position, from which the sample transport device is lowered into a release position, can be performed, wherein in said starting position after lowering a sample can be taken up into the sample transport device, and wherein in said target position after lowering a sample can be released from the sample transport device to said sample holder.

The positioning device 1 further provides the positioning auxiliary device 30 shown in FIG. 6a. The positioning auxiliary device provide means for limiting 40 of the relative mobility of the first and second part in the adjusted target position, means for adjusting 50 of the n-th target position from a plurality of N=12 predetermined target positions as the adjusted target position, means for changing 60 of the adjusted target position from the n-th target position to a (n+1)-th target position and, further, first means for coupling 70 of said a linear translatoric positioning motion P along the x-axis and said positioning device 30, or for coupling of P to the means for changing 60, respectively, such that by means of the first means for coupling 70 (FIG. 6a) the change from said n-th target position to said (n+1)-th target position can be effected during a positioning motion P.

The means for adjusting 50 provides a main element 51 and twelve auxiliary elements 52. The main element 51 is arranged rotatable around the rotation axis 53, and, beyond it, is translatorically unmovable arranged in the direction of the rotation axis 53 with respect to the second part 20, to which it is assigned to. The rotatable main element 51 is firmly connected to the rotation axis 53 via a fixating flange 56. For mounting it to the housing, the rotation axis 53 is pivoted in plastic floating bearings at the housing 104 or the second part 20, respectively, via three bearing elements and, in particular, by means of the flanges 54. Towards the right end face, the rotation axis is firmly connected with the adjustment wheel 106, by means of which a user can adjust a desired target position also independent from the automatic change of positions of the means for changing 60. The adjustment wheel 106 and the means for marking 107 of the adjusted target position are arranged externally form the housing such that the rotation axis 53 provides a sufficiently extended extension rod 55 for extending the rotation axis through the side panel 141 of the housing 104. As shown in FIG. 2a, for example the side panel 141 provides, preferably, a sleeve with a window 107, by means of which the axially adjusted target position can be easily recognized by the user, while the sleeve hides the other markings of the other target positions. This reduces the risk that a user erroneously manually adjusts a wrong adjustment of the desired target position (n+m) by means of the adjustment wheel 106.

The main element 51 is a substantially cylinder-shaped component, with a substantially cylinder-shaped outer surface 57. At the right front face of the main element 51, twelve auxiliary elements 52 are firmly arranged in equidistant distances along a circular distance, which follows a circle, which has a circle centre in the middle point of the rotation axis 53. An auxiliary element 52 is an elongated, rod-like component, which provides a stopping area 40 at its right exterior side, namely a circular stopping surface 40a, which runs perpendicular to the rotation axis 53. The circular stopping surface 40a is assigned to the means for limiting 40, as well as the counter stopping surface 41 at the counter section 42, which is firmly arranged at the first part 10. Adjacent auxiliary elements provide a length difference in x-direction, which exactly corresponds to the desired distance of the target positions, which are to be approached stepwise by means of the translatoric linear position motion P, to be able to stepwise fill, for example, the 12 rows of a 96-well plate.

More precisely, the first part 10 provides a guiding plate 11, which is arranged horizontally and arranged in the inside of the housing, wherein at said guiding plate and the guiding elements 152 (see FIGS. 5a, 5b) can be arranged, by means of which the first part is guided at the second part by the positioning motion P, which runs in parallel to the rotation axis 53 of the drum device 58. The guide plate 11 provides an arm section 12, which extends in direction to the right housing panel 141 horizontally to the right. The designations of directions "right" and "left" are defined in relation to the front view of the pipetting apparatus in FIG. 7 such that the direction "to the right" is the direction along the rotation axis 43 from the left housing panel 143 towards the right housing panel 141 and the direction "of the left" is the opposing direction. An arm part 13, which extends downwards, is firmly and rigidly connected to the horizontal arm section 12. The arm part provides an opening at its lower end, at which an inside thread for the adjustment screw 42 is arranged. In said opening is arranged the counter section 42, which is formed by said adjustment screw 42 with a screw head 43. The adjustment screw 42 provides safe-locking. At its left side the adjustment screw 42 provides the counter stopping surface 41. A n-th target position is characterized by the fact that the guided first part 10 can attach against the stopping surface 40 of the n-th auxiliary element by means of the counter stopping surface 41. At its right side, the counter section 42 provides a rotatable screw head 43, which can be turned by a suitable hexagon socket screw key 49 (FIG. 7), which extends deep into the housing through an opening at the right housing panel 141. Thus, the position of the counter section 42 can be adjusted against the first part by means of the adjustment screw 42, but is firmly arranged at the first part 10.

The means for adjustment 50 are arranged at said second part 20 and contain as the main element, in particular, the rotatable component 51, which is configured as rotatable drum device 58. At the drum device 58 at least parts of said means for limiting 40, 41 are arranged at end parts of said means for changing 60. The drum device 58 provides a substantially cylinder-shape exterior side at which said means for changing 60 are at least partially arranged. Said means for changing 60 are configured, in particular, as a plurality of N=12 guiding grooves 60, which are arranged equidistant and which coil up at said exterior side 57, which are configured angular with respect to the rotation axis 53 and whose open ends are directed in a direction parallel to the rotation axis 53 of the drum device 58. For a better threading of the engagement section 72 into the guiding groove 60, the latter can also be helically shaped, and can provide a starting section, in particular in the direction to the left, which runs substantially in parallel to the rotational axis 53. The guiding grooves 59, 60 are configured for the engagement of the engagement section 72 of an engaging element 71, which is assigned substantially to the first means for coupling 70. The engagement section 72 is pivoted around the E-direction at the engagement element 71, by means of a ball bearing. This way, the engagement section 72 rolls during its motion within a guiding groove 60 along the inside of the same, instead of just sliding there. Thereby the expenditure of energy of a user is reduced, which is required for positioning of the first and second part, because less frictional loss occurs.

The first means for coupling 70 provide an engagement element 71, which is arranged at the first part 10, which can be translatorically moved with its carrier element 73 in the direction of the linear positioning motion P against the second part 20, the engagement element 71 being a further arranged translatorically moveable at the first part 10 in the opening 73a of its carrier element 73, in particular moveably arranged in an engagement direction E, which runs perpendicular to said rotation axis 53 of the drum device 58, the engagement element 71 being further arranged at the first part 10 in the direction parallel to the rotation axis 53 and being further configured for engaging said guiding grooves 60. The guiding device 150, 151, 152 is configured for performing a translatoric relative motion of the first and second part along a linear guiding direction (x-axis), which runs substantially in parallel to said rotation axis such that the engagement of the engagement element 61 into said guiding grooves 59 of the drum device 58 effects that during said substantially translatoric positioning motion the engagement element 61, which engages a guiding groove, turns the drum device 58, which is under forcible control, whereby the change from n-th target position to the (n+1)-th target position occurs and the latter is adjusted as the new adjusted target position. Thereby, the positioning auxiliary device 30, in particular the main element 51, provides a detention device 58, preferably, which is not fully shown in FIGS. 6a and 6b, such that the drum device 58 catches non-permanent in each target position.

The first means for coupling 70 are connected with a second means for coupling 74 (FIG. 6b), which couples the positioning motion P to the first means for coupling 70, 71, such that the first means for coupling 70 are moveable by means of the second means for coupling 74 during a positioning motion. The opening 73a in the carrier element 73 for guiding the moveable engagement element 71 in a direction E perpendicular to the rotational axis 53 is assigned to said second means for coupling 74. The carrier element 73 is rigidly and firmly connected to the plate 11 of the first part. Said second means for coupling 74 are configured for moving the engagement element 71 along said engagement direction E (FIG. 6b). The second means for coupling 74 provide, in particular, a slotted link device 75 and a slide block member 76, wherein the slotted link device 75 is mounted to the second part 20 and is arranged to extends substantially along the linear guiding direction x and position motion P. The slide block member 76 is firmly arranged at the engagement element 71, while it extends substantially perpendicular to the engagement direction E and substantially perpendicular to the rotational axis 53. The slotted link device 75 provides two slotted links 77 and said slide block member 76 provides two slide blocks 78, arranged in distance to each other and guidable by means of said slotted links 77, the sliding blocks 78 being rotatably supported at the slide block member 76, substantially rotatable around the z-axis, by means of a ball bearing, which reduces the frictional resistance during guiding and such reduces the energy required for positioning by the user.

FIG. 6c shows a perspective review of the slotted link device 75, by means of which the linear positioning motion P, shown in FIG. 6b, effects a position-dependent coupling or decoupling of the first means for coupling in the direction E in FIG. 6b. FIG. 6d shows the slotted link 77 of the FIGS. 5a, 5b and 6a to 6c in a top view. The slotted links 77 are both shaped the same and shaped such that the engagement element 71 does not engage said guiding groove 59, 60 during the position motion P from the starting position to the n-th target position and does engage into said guiding groove during the position back motion from the n-th target position in the starting position, whereby on said return path it is changed from the n-th target position to the (n+1)-th target position and the latter being adjusted as the new target position. This is realized by guiding the engagement element 71 by the slide blocks 78 in the slotted link 77, namely during the forward motion PV in direction towards the adjusted target position of the first part 10 along the dashed line, which is further away from the rotation axis 53 of the drum device 58 in a first distance in the broader middle area 77a of the slotted link 77 than the dotted line of the backward motion PR in a shorter second distance from the rotation axis 53. The opening 73a preferably provides locking means to let the engagement element 71 engage at the carrier element 73 in the first distance and the second distance from the rotation axis 53, which stabilizes the respective position, whereby a safe coupling or decoupling into/from the guiding groove 60 is improved. This way, the main element 51 of the drum device 58 is bypassed in the area 77a during the forward motion such that the engagement element 71 does not engage the guiding groove 60. In the area 77b of the slotted link 77 the sliding blocks 76 and thus, the engagement element 71, are shifted in the direction E, and the engagement element 71, which was shifted in this way, engages the guiding groove 60 on the returning path of the first part 10, whereby the drum 58 is rotated. In the area 77c the engagement element 71 has preferably already left the right open end of the guiding groove 60 and is moved away back from the rotation axis 53 of the drum device 58 by the ramp of the slotted link opposite to the direction E. This way, an automatical, stepwise change of the adjusted target position is achieved, without requiring a further user activity in addition to the positioning motion P. The engagement element 71 can also be coupled and decoupled from the guiding grooves 60 by other second means for coupling, in particular by other mechanical means or means with electrical or magnetic function and the like.

FIG. 7 shows perspectively a front view of the sample distribution apparatus of the FIGS. 2a to 2f and the means for fine adjustment 42, 43, 49 of the target positions of the positioning device shown in FIG. 6a. With reference to said drawing and with reference to FIG. 6a, it should be noted that the means for adjustment 50, in particular the drum device 58 and the first means for coupling 70, in particular the engagement element 71, and the second means for coupling 74, in particular the slotted link device 75, can be arranged individually, respectively, and in combination more compact, i.e. within a smaller volume, for example, within a smaller volume, which is smaller by a factor c compared to the volume, shown in the embodiment, wherein c can be, for example, between 0.1 and 0.9, 0.25 and 0.75, or between 0.25 and 0.5.

FIG. 8a shows perspectively a back view of sample distribution apparatus 100', which is also shown in FIGS. 17, 18 and 19 which is equipped with a guiding device 150' according to FIG. 9, in particular with the automatic height adjustment device 180 (as shown in FIG. 8b), which lifts the sample supply container 101 by means of the positioning motion P at a starting position, for adjusting the uptake height with relation of the holding device 130 or the pipette 102, respectively. The height adjustment device 180 comprises the roller element 181, which is arranged rotatable around an rotation axis 183, the roller element being preferably firmly connected to the first part 10 of the positioning device 1" according to the invention. The roller comprises two contact wheels, which are preferably rubber wheels 182 with high friction. As further explained below, the first part 10" of the pipette 102 is unmovable in the x-y-plane at the sample distribution apparatus 100', and is, thus, arranged stationary and is connected to the stationary housing 104".

The height adjustment device 180 further provides a lift device 184, 185. A first lift element 184 is connected with the supply container holding frame 113 and provides a guiding device for a vertical guidance of the second lift element 185. A supply container bearing (not shown), which is arranged within or under the supply container holding frame 113 and can be vertically shifted, is thereby firmly connected to the second lift element 185, which is arranged externally from the holding frame 113, the lift element 185 being vertically moveable at said guiding device. The second lift element 185 provides a ramp-like flat bottom side 186. A positioning motion P effects that the second lift element 185 and the ramp 186, arranged to the lift element 185, attaches on the roller 181 of the first part 10, wherein the second lift element is urged low-friction upwards by the rotating roller 181 by the rotating roller, whereby the supply container bearing automatically moves the supply container 101 in the holding frame 113 upwards into an uptake height or uptake position, respectively, without requiring an additional user activity. FIG. 8*b* shows a detail of FIG. 8*a*.

FIG. 9 shows the guiding device 150', with guiding rails 151' instead of guiding struts 151 and correspondingly configured guiding elements 152', which can be alternatively used in the sample distribution apparatus 100 of the Figures, with detail excerpts. The guiding device 150' provides, in particular, two guiding rails, running horizontally side by side and being arranged in parallel, and further provide two guiding rails, being arranged on top of each other and running in parallel, which renders the guidance of the guided other part, which is correspondingly configured, particularly stable. Preferably, only one guiding rail or guiding strut, which is arranged under the over plate 105, and only one guiding rail or guiding strut, which is arranged laterally to the first rail or strut, are provided. Preferably, in total at least three or, preferably, exactly three guiding elements are provided, because the use of three guiding elements achieves a stable three-point bracing of the first part against the second part at two guiding rails or guiding struts, which are arranged in distance, under a, preferably, minimal friction of the guidance.

FIGS. 10*a* and 10*b* show perspectively in a top view the holding device with the pipette of the sample distribution apparatus of the FIGS. 2*a* to 2*f*, which is arranged above the sample holder device, which is equipped with a 384-well plate 103', showing the arrangement in a 0°-arrangement of the well plate and in a 180°-arrangement of the well plate. By means of an arrangement of the well plate 103 in the sample distribution apparatus 100, 100', which is configured for the equipment with 96-well plates, the arrangement providing a rotation of 180° in the x-y-plane, it is achieved that also 384-well plates can be filled by means of the same apparatus by an 8-channel pipette 102, which is effected by the configuration of the well plates. Since the distance of the sample wells of the 384-well plate corresponds to half of the distance of the 96-well plates, and since the sample well-array of the 384-plate is asymmetrically arranged with respect to outer edges of the 384-plate, namely asymmetrically different about a distance corresponding to a row distance of the 384-plate, it becomes possible to fill in the 0°-position the rows and columns with uneven number and in the 180°-position the rows and columns with even number.

Figure 11A:
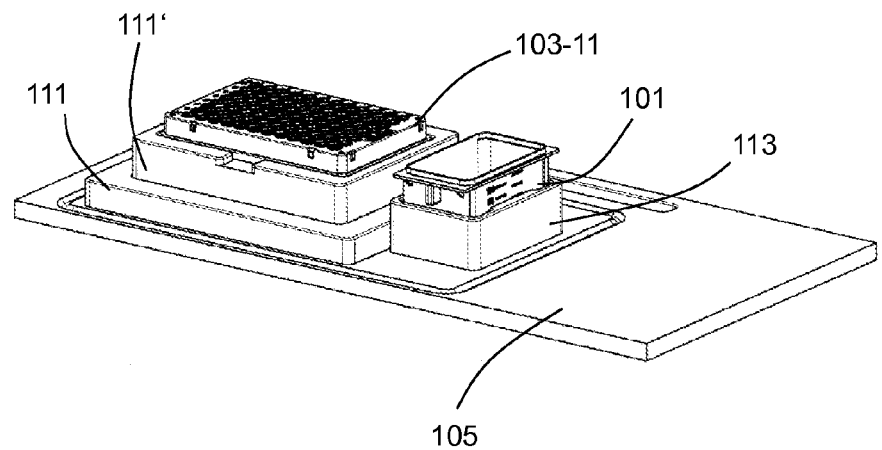
Figure 11B:
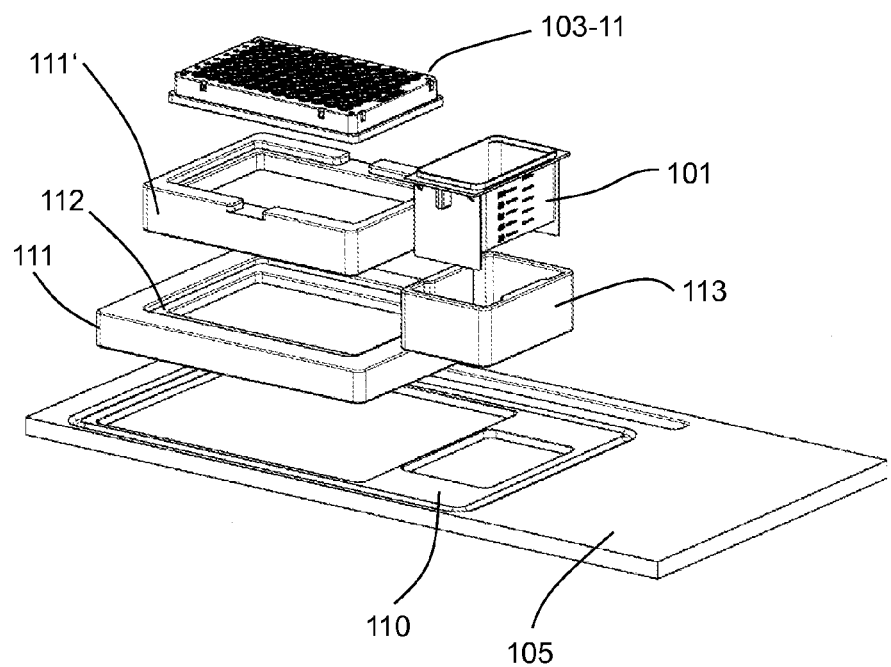
Figure 12A:
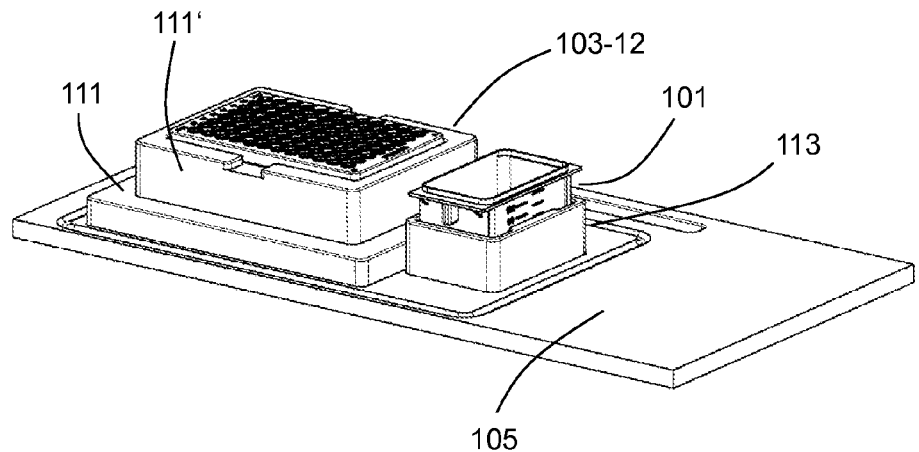
Figure 12B:
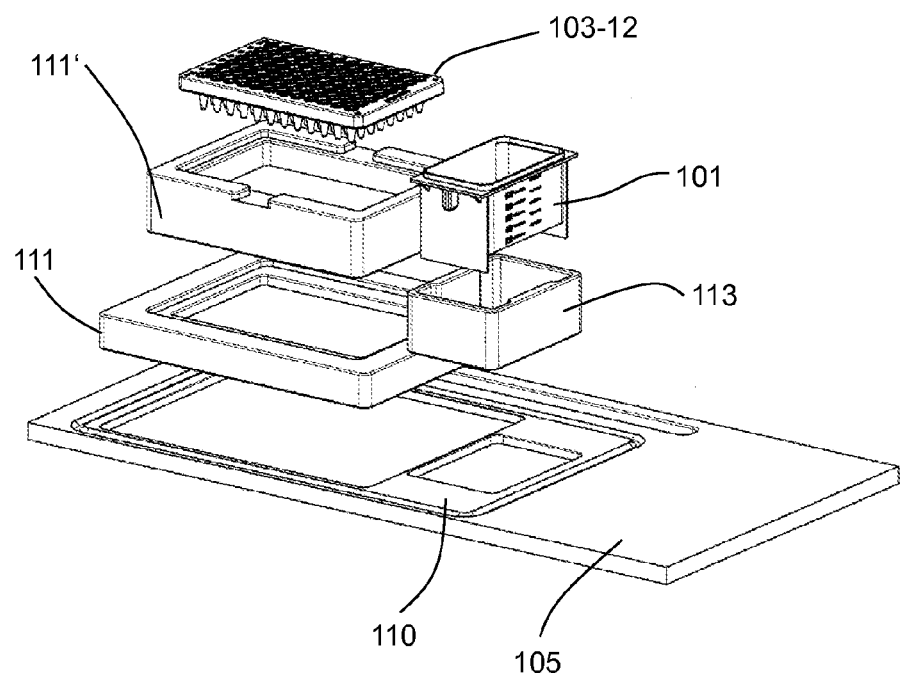
Figure 13A:
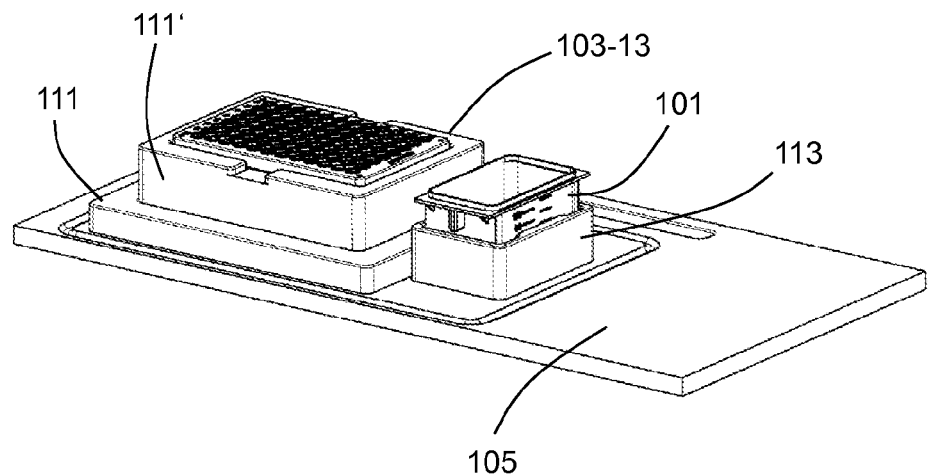
Figure 13B:
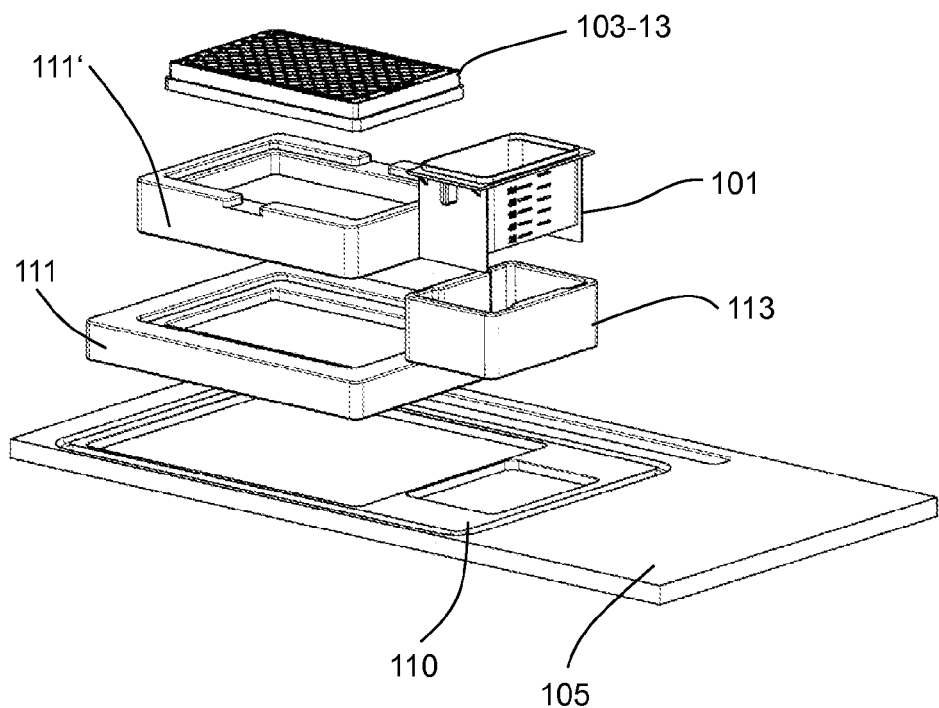
Figure 14A:
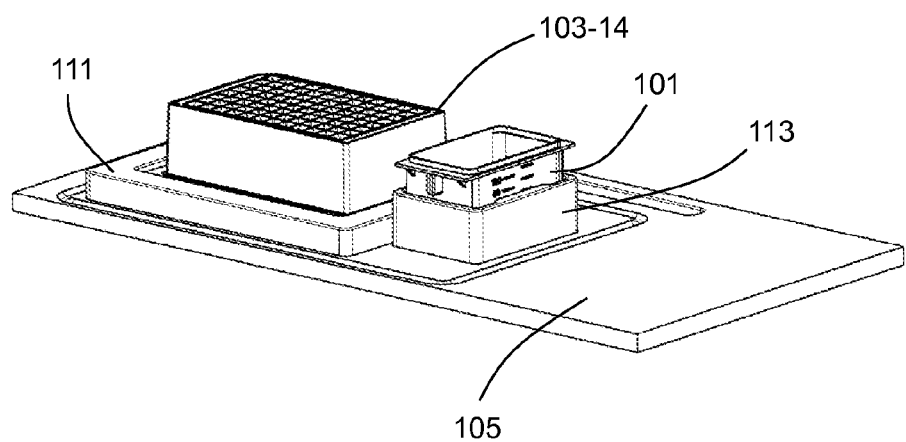
Figure 14B:
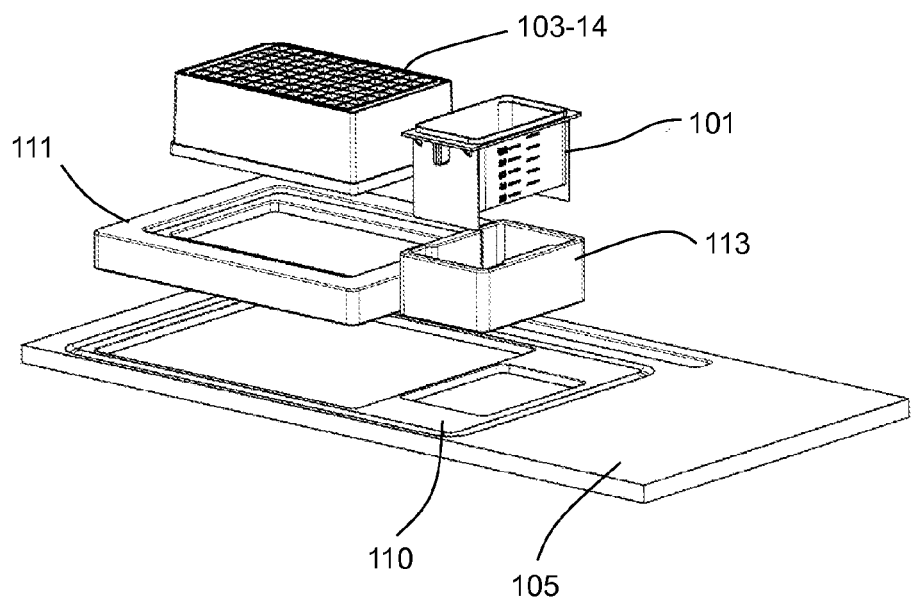
Figure 15A:
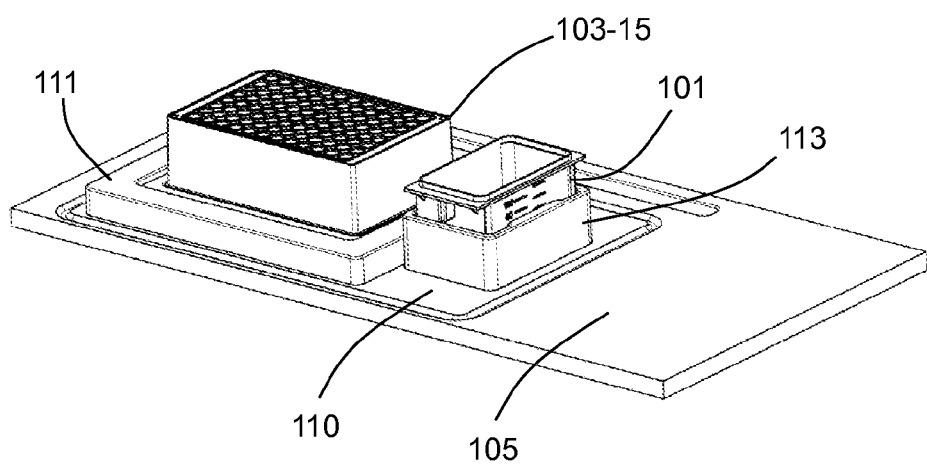
Figure 15B:
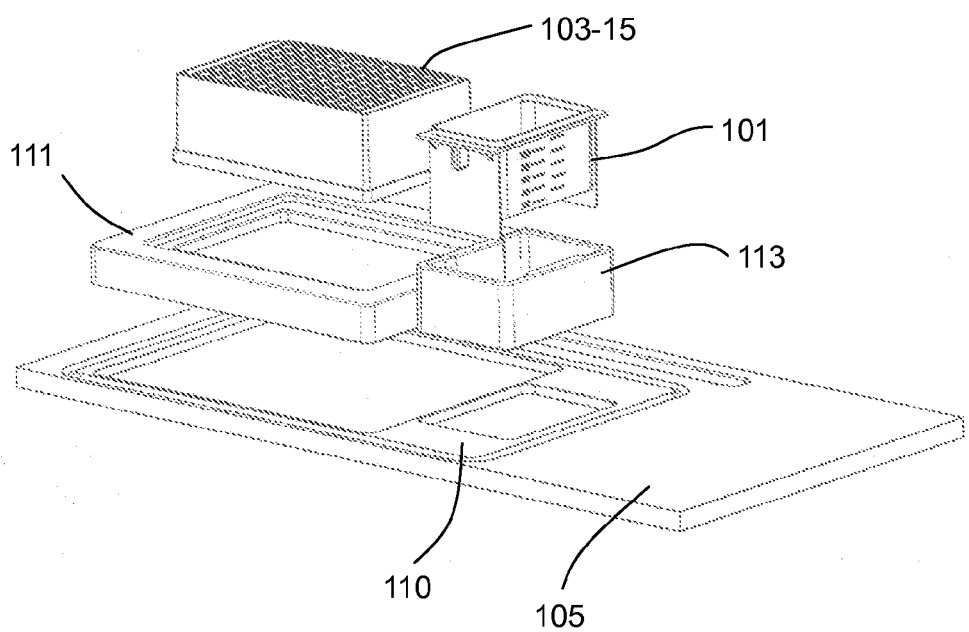

FIGS. 11*a* to 16*b* show six different embodiments of adapter elements for the sample holder device of the sample distribution apparatus of FIGS. 2*a* to 2*f*, for six different sample holder embodiments, namely in perspectively isometric view (FIGS. 11*a*, 12*a*, 13*a*, 14*a*, 15*a*, 16*a*) or an perspective exploded view (FIGS. 11*b*, 12*b*, 13*b*, 14*b*, 15*b*, 16*b*). For narrow sample plates, additional adapter frames 111' can be provided, to ensure an unitary height of the upper side of the sample plate, if the same is arranged in the holding device, for being filled. FIGS. 11*a*, 11*b* show the cover plate 105, in whose largest recess the adapter 111 is arranged and laterally fixated, wherein a second adapter frame 111' is provided, which is arranged in the second recess of the adapter frame and is laterally fixated. The second adapter frame brings the upper side of a well plate 103-11 to a standard height, to which the pipetting apparatus 100 is configured. FIG. 12*a*, 12*b* show a similar arrangement with another well plate 103-12 with another second adapter frame 111'. FIGS. 13*a*, 13*b* show a similar arrangement with another well plate 103-13 with another second adapter frame 111'. FIGS. 14*a*, 14*b* show an arrangement with another well plate 103-14 (of type Eppendorf Deepwell Plate® with quadratically shaped sample wells) with the first adapter frame 111, only, which is adapted to the height of the deep well plate 103-14. Said arrangement corresponds to the arrangement of the cover plate 105, adapter frame 111 and well plate 103 (Deepwell with circular-shaped sample wells), as shown in FIGS. 2*a* to 2*f*, which is again as shown in FIG. 15*a*, 15*b* more in detail.

FIG. 16*a* shows an embodiment of an alternative sample supply container, which can be used with the sample distribution apparatus of FIGS. 2*a* to 2*f*. FIG. 16*b* shows the sample supply container shown in FIGS. 2*a* to 2*f*.

FIGS. 17 to 19 show a second embodiment 100' of the sample distribution apparatus according to the invention with a positioning device 1" according to the invention, with a second part 20", which is moveable against the stationary housing, and with an substantially unmovable first part 10", and with otherwise substantially similar components, which are already provided by the embodiment 100 according to the FIGS. 2*a* to 2*f*. The first part 10" is arranged translatorically unmovable in x-y-plane at the stationary housing 104" of the sample distribution apparatus 100'. The latter provides a sample holder arrangement section 105", which is translatorically moveable along the x-axis, and which provides a sample holder receiving plate 105*a*". Within the latter, the well plate 103 is laterally fixated, but is arranged to be removable in upward direction. By means of the left handle 105*b*" or the right handle 105*c*", which are firmly connected to the sample holder arrangement section 105", respectively, the second part 20" can be shifted against the first part 10" by means of the linear positioning motion P, along the guiding direction of the x-axis, which is determined by the arrangement of the guiding rails 151". Further, the second part 20" provides the sample supply container 101", which is arranged laterally, i.e. in the x-y-plane, unmovable at the second part 20", but which can be moved along the z-axis by the bearing at the sample supply container holder 113" via a vertical guiding device 101*a*", which allows an automatical height adjustment of the sample supply container, if the second part 20" is moved to a starting position (uptake position). The functionality of the automatical height adjustment device has already been explained above with reference to the FIGS. 8*a* and 8*b*.

The pipette 102, the sample holder device 130", the vertical member 120", the means for adjustment 50", i.e., in particular, the drum device 58" with N=12 auxiliary elements 52", as well as the rotation axis 53", its bearing elements 54" and 56" as well the housing 104" are assigned to the stationary first part 10". The pipette holder 131" and the bearing sections 135" and 136", which is firmly connected to the pipette holder, and the pipette 102, which is fixated to the bearing sections by the screws 135*a*""", are arranged to be moved along the z-axis via height adjustment device 130''', namely within the limits, which are predetermined by the two stopping elements 130a'' and 130b''. Stopping elements 130a'' and 130b'' are two screws, whose position can be changed along the z-axis at the vertical member 120'' by turning, whereby a change of position of the stopping areas is achieved. This allows an adjustment of the vertical movability of the pipette holder 131'', 135'', 136'' such that the apparatus can be used in flexible way.

Front panel 142'' of the housing 104'' provides a recess 142a''. The carrier element 73'', which is firmly connected to the moveable second part 20'', can be moved along said recess 142a'', the carrier element 73'' carrying an engagement element 71'', which is supported at the carrier element 73'' moveable in the direction of the y-axis. The engagement element 71'' is guided by forcible control of the slotted links 77'' of the slotted link device 75'' and the coupling and decoupling of the engagement element 71'' in the guiding groove 60'' of a drum device 58'' is effected by the shape of the slotted link 77'', which substantially corresponds to the shape of the slotted link 77 of the sample distribution apparatus 100. This can be particularly well understood with reference to FIG. 18.

FIG. 18 shows a top view on the components of the positioning auxiliary device 30'' of the positioning device 1''. The components shown and their functionality corresponds, substantially, to the corresponding, equally designated components of the sample distribution apparatus 100 and the positioning device 1, which is shown, for example, in FIGS. 6a to 6d. In case of the sample distribution apparatus 100', a target position is approached, if the user shifts the second part 20'' to the right until the counter section 42'', being attached to the second part 20'', the counter section 42'' being arranged adjustable along its position with respect to the second part 20'' along the x-axis by the manual adjustment screw 42'', attaches on the stopping surface 58'' of an auxiliary element 52'' with its counter stopping surface 51'', the auxiliary element 52'' being arranged translatorically unmovable in the direction of the x-axis, but being arranged rotatable around the rotation axis 53'' (x-axis) via the drum device 58'' and its rotation axis 53, which are firmly supported at the stationary housing 104'' by the bearing elements 54'' and 56''. Similar to the positioning auxiliary device 30, the engagement element 71'' engages the guiding groove 60'' of the drum device 58'' upon motion of the moveable second part 20'' in the case of the positioning auxiliary device 30'', whereby the drum device is rotated by one step. This way, the automatic change from the n-th to the (n+1)-th target position is realized, by letting the user merely performing the positioning motion as the actuation, which automatically effects the change by the first means for coupling.

The invention claimed is:

1. Positioning device (1; 1') for a sample distribution apparatus (100; 100', 200) providing:
 a first part (10; 10'), configured such that a sample transport device (102) is arranged at the first part,
 a second part (20; 20'), configured such that a sample holder (103; 103') is arranged at the second part,
 wherein the first part and the second part are arranged moveable relative to each other between a first position and an adjusted target position of the first and the second part for performing a positioning motion,
 wherein an actuation motion is provided, which serves the conveyance of the sample,
 a positioning auxiliary device (30; 30'),
 which provides at least one means for limiting (40; 40') of the relative mobility of the first and the second part in the adjusted target position,
 which provides at least one means for adjustment (50; 50') of the n-th target position from a plurality of N predetermined target positions as the adjusted target position,
 which provides at least one means for changing (60; 60') of the adjusted target position from the n-th target position to a (n+1)-th target position, and
 which provides at least one first means for coupling (70; 70') of the actuation motion and the at least one means for changing such that the change from said n-th target position to said (n+1)-th target position can be effected by the actuation motion via the at least one means for coupling,
 wherein the positioning device is configured such that the n-th target position is adjusted, before the positioning motion of the first and the second part into the n-th target position is finished.

2. Positioning device according to claim 1, characterized in that the actuation motion is said positioning motion.

3. Positioning device according to claim 1, characterized in that the actuation motion is a motion, which is manually conducted by user.

4. Positioning device according to claim 1, characterized in that a plurality of N means for limiting are provided, by means of which N target positions can be adjusted.

5. Positioning device according to claim 1, characterized in that the positioning device provides a guiding device, by means of which a guided positioning motion of the first and the second part relative to each other between a first position and an n-th target position can be conducted.

6. Positioning device according to claim 5, characterized in that said guiding device is configured for performing a translatoric relative motion of the first and second part along a linear guiding direction, which runs substantially in parallel to said rotation axis such that the engagement of the engagement element into said guiding grooves of a drum device effects that the engagement element, which engages the guiding groove, rotates the drum device during said substantially translatoric positioning motion, whereby it is changed from the n-th target position to the (n+1)-th target position and the latter is adjusted to be a new adjusted target position.

7. Positioning device according to claim 1, characterized in that the at least one first means for coupling is mechanically such that it mechanically effects the change from said n-th target position to said (n+1)-th target position during the positioning motion.

8. Positioning device according to claim 1, characterized in that the at least one means for limiting, the at least one means for adjustment and the at least one means for changing are operating mechanically.

9. Positioning device according to claim 1, characterized in that the at least one means for limiting provide a plurality of N stopping areas, at which the motion of the first and second part in a motion direction is blocked by attachment of both parts, if they are guided from the first position in the direction of a target position.

10. Positioning device according to claim 9, characterized in that a counter stopping area is assigned to the positioning auxiliary device, the counter stopping area being arranged at the first part such that the relative motion of the first and the second part can be blocked by the attachment of an n-th stopping area at said counter stopping area.

11. Positioning device according to claim 10, characterized in that the positioning auxiliary device provides a means for a manual adjustment of the position of the counter stopping area in relation to the first part.

12. Positioning device according to claim 1, characterized in that the at least one means for coupling are moveably arranged at the first part and that the positioning auxiliary device provides also at least one second means for coupling the positioning motion to the at least one first means for coupling such that the at least one first means for coupling is moveable by the at least one second means for coupling during a positioning motion.

13. Positioning device according to claim 12, characterized in that the at least one second means for coupling is configured for moving an engagement element along an engagement direction, whereby the means include a slotted link device and a slide block member, whereby the slotted link device is arranged at the second part and is arranged extending substantially along a linear guiding direction and the slide block member being arranged substantially extending perpendicular to the engagement direction and substantially perpendicular to a rotational axis, arranged firmly to the engagement element.

14. Positioning device according to claim 13, characterized in that said slotted link device provides a slotted link and said slide block member provides a sliding block which can be guided through the slotted link, wherein the slotted link is shaped such that the engagement element does not engage into a guiding groove during the positioning motion from the first position to the n-th target position and does engage into a guiding groove during the positioning back motion from the n-th target position to the first position, whereby it is changed during the return path from the n-th target position to the (n+1)-th target position and the latter being adjusted as a new target position.

15. Positioning device according to claim 1, characterized in that in at least one means for adjusting are arranged at the second part and include a rotatable drum device, at which the at least one means for limiting and the at least one means for changing are arranged.

16. Positioning device according to claim 15, characterized in that the drum device provides a substantially cylinder-shaped exterior side and that the at least one means for changing provides a plurality of N helically-shaped guiding grooves, which coil up at said exterior side and are arranged equidistant, wherein the open ends of said guiding grooves are directed in the direction of the rotation axis of the drum device.

17. Positioning device according to claim 16, characterized in that the at least one first means for coupling comprises an engagement element, which is arranged at the first part, which is arranged moveable in a engagement direction perpendicular to a rotation axis at the first part, and is arranged unmovable in the direction of the rotation axis, and which is configured for engaging said guiding grooves.

18. Positioning device according to claim 1, characterized in that the first part is arranged moveable and that the second part is arranged unmovable at the sample distribution apparatus or that the first part is arranged unmovable at the sample distribution apparatus and the second part is arranged moveable.

19. Positioning device according to claim 1, characterized in that the first part can be manually moved in relation to the second part by a user.

20. Positioning device according to claim 1, characterized in that the positioning auxiliary device provides means for a manual adjustment of the n-th target position from a plurality of N predetermined target positions.

21. Positioning device according to claim 1, characterized in that the positioning device comprises spring means for the suspension of the relative motion of the first and second part, once the relative motion approaches the n-th target position.

22. Sample distribution apparatus with a positioning device according to claim 1, wherein the positioning device provides a first part, at which a holding device for holding of a sample transport device is arranged, provides a second part, which is moveably arranged in relation to the first part and at which a sample holder can be arranged, wherein the first part and the second part are moveably arranged in relation to each other between a first position and an adjusted target position of the first and second part for the performance of a positioning motion, and provides an inclination apparatus, by means of which the holding device for holding the sample transport device is arranged to be inclined against the first part.

23. Sample distribution apparatus according to claim 22, characterized in that third means for coupling of the positioning motion and said means for changing are provided such that a change of the height of the supply container holder is effected during the approaching of a starting position.

24. Sample distribution apparatus configured to be a pipetting apparatus, which provides a positioning device according to any one of claim 21.

25. Sample distribution apparatus according to claim 24, wherein the positioning device provides a first part, at which a sample transport device can be arranged, provides a second part, which is moveably arranged in relation to the first part and at which a sample holder can be arranged, wherein the first part and the second part are moveably arranged relative to each other between a first position and an adjusted target position for the performance of a positioning motion such that a sample is conveyable against the sample holder by the positioning motion between the first position and the adjusted target position and is conveyable at the target position by release from the sample transport device to the sample holder, wherein an actuation motion is provided, which serves the conveyance of the sample,
    wherein the sample distribution apparatus further provides an automatic height adjustment device, at which a height adjustable component of the apparatus is automatically adjusted in height by the actuation motion.

26. Sample distribution apparatus according to claim 24, characterized in that the first part is configured for holding a sample transport device, which is a commercially available hand-operated pipette or a commercially available hand-operated dispenser.

27. Method for positioning a first part relative to a second part in subsequent steps at, respectively, different target positions by means of a sample distribution apparatus according to claim 24 comprising the steps, that an n-th positioning motion of the first and the second part relative to each other is performed between the first position and the predetermined n-th target position, the n-th target position being adjustable at the positioning device as one of N possible predetermined target positions, that a subsequent (n+1)-th positioning motion of the first and the second part relative to each other is performed between the first position and the (n+1)-th target position, by utilizing an actuation motion to effect the change from the n-th target position to the (n+1)-th target position by the coupling of the actuation motion with the positioning auxiliary device such that the (n+1)-th target position is adjusted as said new adjusted target position.

28. Method for positioning a first part relative to a second part in subsequent steps at, respectively, different target positions by means of a positioning device according to any one of claims 1 to 21, comprising the steps,
    that an n-th positioning motion of the first and the second part relative to each other is performed between the first position and the predetermined n-th target position, the n-th target position being adjustable at the positioning device as one of N possible predetermined target positions, that a subsequent (n+1)-th positioning motion of the first and the second part relative to each other is automatically performed between a first position and the (n+1)-th target position, by utilizing an actuation motion to effect the change from the n-th target position to the (n+1)-th target position by the coupling of the actuation motion with the positioning auxiliary device such that the (n+1)-th target position is adjusted as said new adjusted target position.

29. Method according to claim 28, wherein the return path of the n-th positioning motion from said n-th target position back to the first position is utilized to effect said change from the n-th target position to the (n+1)-th target position by a coupling of the positioning back motion with the positioning auxiliary device such that the (n+1)-th target position is adjusted as said new adjusted target position.

* * * * *